(12) United States Patent
Morimoto et al.

(10) Patent No.: US 11,369,403 B2
(45) Date of Patent: Jun. 28, 2022

(54) HANDHELD INSTRUMENT FOR ENDOSCOPE SURGERY

(71) Applicant: SONY CORPORATION, Tokyo (JP)

(72) Inventors: Rui Morimoto, Kanagawa (JP); Kazuhiko Miyahara, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 527 days.

(21) Appl. No.: 15/774,382

(22) PCT Filed: Nov. 29, 2016

(86) PCT No.: PCT/JP2016/005009
§ 371 (c)(1),
(2) Date: May 8, 2018

(87) PCT Pub. No.: WO2017/094257
PCT Pub. Date: Jun. 8, 2017

(65) Prior Publication Data
US 2020/0246041 A1    Aug. 6, 2020

(30) Foreign Application Priority Data

Nov. 30, 2015  (JP) .............................. JP2015-233108
Apr. 5, 2016   (JP) ................................ 2016-075701

(51) Int. Cl.
*A61B 17/32*   (2006.01)
*A61B 8/00*    (2006.01)
(Continued)

(52) U.S. Cl.
CPC ........ *A61B 17/320092* (2013.01); *A61B 8/12* (2013.01); *A61B 8/445* (2013.01);
(Continued)

(58) Field of Classification Search
CPC .... A61B 17/320092; A61B 2017/0011; A61B 2017/2825; A61B 2017/320088; A61B 2017/320094; A61B 8/12; A61B 8/445
See application file for complete search history.

(56) References Cited

U.S. PATENT DOCUMENTS 4,651,850 A * 3/1987 Matsuo ................. G10K 11/30
                                                     181/175
5,174,295 A * 12/1992 Christian ................ A61B 8/06
                                                     600/468
(Continued)

FOREIGN PATENT DOCUMENTS

CN    101023883 A    8/2007
EP     1762190 A2    3/2007
(Continued)

OTHER PUBLICATIONS

International Search Report and Written Opinion of PCT Application No. PCT/JP2016/005009, dated Feb. 28, 2017, 11 pages of ISRWO.

(Continued)

*Primary Examiner* — Pascal M Bui Pho
*Assistant Examiner* — Alexei Bykhovski
(74) *Attorney, Agent, or Firm* — Chip Law Group

(57) ABSTRACT

A handheld instrument for endoscope surgery includes a shaft, a jaw, a handle, a phased array ultrasonic sensor, and a signal wiring. The jaw is placed at one end of the shaft and has a holding function. The handle is placed at the other end of the shaft and includes an operation mechanism for operating the jaw. The phased array ultrasonic sensor is mounted on the jaw and has an imaging function. The signal wiring is provided to the shaft and connects the ultrasonic sensor and the handle.

24 Claims, 18 Drawing Sheets

(51) Int. Cl.
*A61B 8/12* (2006.01)
*A61B 17/00* (2006.01)
*A61B 17/28* (2006.01)

(52) U.S. Cl.
CPC ............ *A61B 2017/0011* (2013.01); *A61B 2017/2825* (2013.01); *A61B 2017/320088* (2013.01); *A61B 2017/320094* (2017.08)

(56) References Cited

U.S. PATENT DOCUMENTS

| | | | | |
|---|---|---|---|---|
| 5,368,036 | A | * | 11/1994 | Tanaka ............... A61B 8/12 600/104 |
| 5,546,947 | A | * | 8/1996 | Yagami .............. A61B 8/12 600/466 |
| 5,865,361 | A | | 2/1999 | Milliman et al. |
| 6,467,138 | B1 | * | 10/2002 | Aime ............... G10K 11/002 29/25.35 |
| 6,569,178 | B1 | * | 5/2003 | Miyawaki ...... A61B 17/320092 606/169 |
| 6,668,664 | B1 | * | 12/2003 | Ohkawa ............. G01F 1/662 73/861.27 |
| 6,896,653 | B1 | * | 5/2005 | Vail, III ............. A61B 1/303 600/109 |
| 2001/0025184 | A1 | * | 9/2001 | Messerly ...... A61B 17/320092 606/169 |
| 2002/0091382 | A1 | * | 7/2002 | Hooven ............. A61B 18/14 606/41 |
| 2003/0013960 | A1 | | 1/2003 | Makin et al. |
| 2007/0191828 | A1 | | 8/2007 | Houser et al. |
| 2008/0195017 | A1 | * | 8/2008 | Robinson .......... A61F 13/0203 602/44 |
| 2009/0275865 | A1 | | 11/2009 | Zhao et al. |
| 2010/0280316 | A1 | * | 11/2010 | Dietz ............... A61M 25/0074 600/109 |
| 2012/0123352 | A1 | * | 5/2012 | Fruland ............. A61B 8/445 604/264 |
| 2014/0001866 | A1 | | 1/2014 | Abe et al. |
| 2014/0018668 | A1 | * | 1/2014 | Zheng ............... A61B 8/488 600/424 |
| 2016/0030077 | A1 | | 2/2016 | Durvasula et al. |
| 2016/0066916 | A1 | * | 3/2016 | Overmyer ........... H02H 3/06 227/176.1 |

FOREIGN PATENT DOCUMENTS

| | | |
|---|---|---|
| EP | 1820460 A2 | 8/2007 |
| EP | 1974771 A1 | 10/2008 |
| EP | 2289443 A2 | 3/2011 |
| JP | 60-86311 U | 6/1985 |
| JP | 2001-517473 A | 10/2001 |
| JP | 2004-532691 A | 10/2004 |
| JP | 2005-218519 A | 8/2005 |
| JP | 2007-229454 A | 9/2007 |
| JP | 2009-523507 A | 6/2009 |
| JP | 2010-131408 A | 6/2010 |
| JP | 2011-139912 A | 7/2011 |
| JP | 2011-525842 A | 9/2011 |
| JP | 2012-511400 A | 5/2012 |
| WO | 99/15086 A1 | 4/1999 |
| WO | 92/096507 A2 | 12/2002 |
| WO | 2007/082422 A1 | 7/2007 |
| WO | 2012/108295 A1 | 8/2012 |
| WO | 2014/164643 A1 | 10/2014 |

OTHER PUBLICATIONS

Office Action for JP Patent Application No. 2017-553628 dated Dec. 8, 2020, 07 pages of Office Action and 07 pages of English Translation.

* cited by examiner

HANDHELD INSTRUMENT FOR ENDOSCOPE SURGERY

CROSS REFERENCE TO RELATED APPLICATIONS

This application is a U.S. National Phase of International Patent Application No. PCT/JP2016/005009 filed on Nov. 29, 2016, which claims priority benefit of Japanese Patent Application No. JP 2015-233108 filed in the Japan Patent Office on Nov. 30, 2015 and also claims priority benefit of Japanese Patent Application No. JP 2016-075701 filed in the Japan Patent Office on Apr. 5, 2016. Each of the above-referenced applications is hereby incorporated herein by reference in its entirety.

TECHNICAL FIELD

The present technology relates to a handheld instrument for endoscope surgery used for surgery using an endoscope.

BACKGROUND ART

In endoscopic surgery such as laparoscopic surgery and thoracoscopic surgery, an opening (port) is provided in a body surface of a patient and a handheld instrument for surgery, an endoscope, or the like is inserted into the body of the patient to perform surgery. As means for observing the inside of the body of the patient, ultrasonic imaging is used in addition to the endoscope in some cases.

In the ultrasonic imaging, ultrasonic waves are irradiated onto an observation object from an ultrasonic probe including an ultrasonic transducer array, and the ultrasonic probe detects reflected waves therefrom to generate an ultrasonic image of the observation target. The ultrasonic imaging is capable of seeing through biological tissues, and suitable for grasping running of blood vessels, and position and shape of tumors, finding nerves, and the like.

However, in the case of using the ultrasonic imaging, it is necessary to provide a port for the ultrasonic probe in a body surface of the patient. Further, since the insertion positions of an incision tool and the ultrasonic probe differ, there is a high possibility that organ positions before and after incision differ, which causes a problem that the position seen through by ultrasonic waves does not match with the place to be actually incised.

In this regard, mounting a sensor for ultrasonic imaging on a handheld instrument for surgery makes it unnecessary to provide a port for the sensor and makes no difference between the insertion positions of the handheld instrument for surgery and the sensor. As an example of mounting a sensor on a handheld instrument for surgery, an instrument for surgery that includes a pressure sensor mounted at the tip of a holding device thereof and is capable of acquiring spatial distribution of blood flow is disclosed in Patent Literature 1.

CITATION LIST

Patent Literature

Patent Literature 1: Japanese Unexamined Patent Application Publication No. 2012-511400

DISCLOSURE OF INVENTION

Technical Problem

However, it is not easy to mount a sensor for ultrasonic imaging on a handheld instrument for endoscopic surgery. In general, in a handheld instrument for surgery having a holding function, the footprint that an ultrasonic sensor can be mounted is only approximately 2 mm×10 mm. When an ultrasonic sensor is mounted on such an area, since the opening diameter is reduced (center frequency of ultrasonic vibration is increased) and the beam of ultrasonic waves easily spreads, the spatial resolution is reduced.

Further, in the case where the thickness of the ultrasonic transducer array is large, the handheld instrument for surgery gets caught when being taken in and out from a trocar (instrument for inserting surgical instruments into the abdominal cavity or the thoracic cavity), and the operability of the handheld instrument for surgery is significantly reduced. For that reason, an ultrasonic transducer array that has a reduced height and causes no problem in taking a handheld instrument for surgery in and out from the trocar is desired.

In view of the circumstances as described above, it is an object of the present technology to provide a handheld instrument for endoscope surgery having an ultrasonic imaging function with a practicable spatial resolution.

Solution to Problem

In order to achieve the above-mentioned object, a handheld instrument for endoscope surgery according to an embodiment of the present technology includes: a shaft; a jaw; a handle; a phased array ultrasonic sensor; and a signal wiring.

The jaw is placed at one end of the shaft and has a holding function.

The handle is placed at the other end of the shaft and includes an operation mechanism for operating the jaw.

The phased array ultrasonic sensor is mounted on the jaw and has an imaging function.

The signal wiring is provided to the shaft and connects the ultrasonic sensor and the handle.

A phased array ultrasonic sensor in which a phased array includes an ultrasonic transducer is capable of generating an ultrasonic image with a high spatial resolution. By mounting this phased array ultrasonic sensor on the jaw having a holding function, it is possible to hold biological tissues and acquire an ultrasonic image by the jaw. As a result, since it is unnecessary to provide a port for an ultrasonic sensor and the insertion position of the jaw into the body and the insertion position of the ultrasonic sensor match with each other, it is possible to provide high convenience.

The signal wiring is a flexible printed circuit board, and the handheld instrument for endoscope surgery may further include a sealing member for sealing a portion of the signal wiring led out from the jaw.

The ultrasonic sensor for the ultrasonic imaging includes many (e.g., dozens to thousands) ultrasonic transducers. Since it is necessary to connect the signal wiring to the individual ultrasonic transducers, a flexible printed circuit board capable of arranging a large number of wirings is suitable for the signal wiring of the ultrasonic sensor. Further, by sealing the portion of the signal wiring led out from the jaw with the sealing member, it is possible to prevent liquid (blood or the like) from entering the ultrasonic sensor mounted on the jaw.

The handheld instrument for endoscope surgery may further include a covering member for covering a part of the signal wiring, the part of the signal wiring extending between the jaw and the shaft.

The part of the signal wiring extending between the jaw and the shaft is exposed from the jaw and the shaft, and bends with opening and closing of the jaw. By covering this part with the covering member, it is possible to protect the signal wiring and suppress disconnection and the like.

The signal wiring may be placed on an outer peripheral surface of the shaft.

Since an operation transmission mechanism for driving the jaw, and the like are provided inside the shaft, it is difficult to pass the signal wiring inside the shaft. However, by placing the signal wiring on the outer peripheral surface of the shaft, it is possible to connect the jaw and the handle with the signal wiring.

The shaft may be formed of a metal, and electrically fixed at ground potential.

The signal for the ultrasonic imaging flowing through the signal wiring is a weak signal of approximately several $\mu V$, and susceptible to noise. However, by electrically fixing the shaft at ground potential, it is possible to suppress generation of external noise.

The handheld instrument for endoscope surgery may further include a protective member that is a tubular member formed of a metal and covers the signal wiring.

By covering the signal wiring with the protective member, it is possible to protect the signal wiring from contact with another handheld instrument for surgery or the like.

The protective member may be electrically fixed at ground potential.

By electrically fixing the protective member at ground potential, it is possible to suppress generation of external noise.

The handheld instrument for endoscope surgery may further include a protective member including a metal layer covering the signal wiring, and a protective layer covering the metal layer.

By covering the signal wiring with the protective member, it is possible to protect the signal wiring from contact with another handheld instrument for surgery or the like.

The metal layer may be electrically fixed at ground potential.

By electrically fixing the metal layer of the protective member at ground potential, it is possible to suppress generation of external noise in the signal wiring.

The handle may further include a rotation knob for rotating the shaft, the rotation knob may have an introduction hole, and the signal wiring may be introduced from the handle into the shaft via the introduction hole.

With this configuration, it is possible to introduce the signal wiring from the handle into the shaft via the rotation knob.

The signal wiring may be a flexible printed circuit board, the handheld instrument for endoscope surgery may further include a sealing member for sealing a portion of the signal wiring led out from the jaw, the signal wiring may be placed on an outer peripheral surface of the shaft, the handle may further include a rotation knob for rotating the shaft, the rotation knob may have an introduction hole, and the signal wiring may be introduced from the handle into the shaft via the introduction hole.

The phased array ultrasonic sensor may include an acoustic lens formed of a material having an acoustic impedance of not less than 1.35 M rayls and not more than 1.74 M rayls.

With this configuration, since the acoustic impedance of the acoustic lens is substantially the same as the acoustic impedance of a living body to be brought into contact with the acoustic lens, it is possible to reduce the thickness of the acoustic lens.

The phased array ultrasonic sensor may include a backing layer formed of a material having an acoustic impedance of 2.05 M rayls.

With this configuration, by using the backing layer as an alternative to a dematching layer (layer that has an acoustic impedance higher than that of a piezoelectric material constituting an ultrasonic transducer and reflects sound waves toward the backing layer), even in the case where the thickness of the backing layer is reduced, it is possible to improve the sound attenuation performance of the backing layer without using the dematching layer.

The phased array ultrasonic sensor may include a backing layer formed of a material having an acoustic attenuation constant of not less than 2.29 dB/MHz/mm.

With this configuration, the reverberation component generated by reducing the thickness of the backing layer can be absorbed by the backing layer, and it is possible to suppress ring-down artifact (virtual image created by reverberation) and background noise.

The backing layer may be formed of polyurethane.

Since polyurethane has an acoustic impedance of not more than 2.05 M rayls and an acoustic attenuation constant of not less than 2.29 dB/MHz/mm, it is possible to reduce the thickness of the backing layer by using polyurethane as the material of the backing layer.

The phased array ultrasonic sensor may include an acoustic lens formed of a material having an acoustic impedance of not less than 1.35 M rayls and not more than 1.74 M rayls, and a backing layer formed of a material having an acoustic impedance of not more than 2.05 M rayls.

With this configuration, as described above, it is possible to reduce the thicknesses of the acoustic lens and the backing layer, and reduce the height of the phased array ultrasonic sensor. For example, the thickness from the backing layer to the acoustic lens can be reduced to not more than 2 mm.

The jaw may include a jaw main body connected to the shaft, a casing that is mounted on the jaw main body and houses phased array ultrasonic sensor, and a tissue pad mounted on a side of the jaw main body opposite to the casing.

With this configuration, since the phased array ultrasonic sensor is housed in the casing, the electronic material constituting this ultrasonic sensor is prevented from being exposed, and the biocompatibility of the jaw is maintained. Further, since the tissue pad is provided, the influence of friction and heat on the ultrasonic sensor is reduced. Since the holding function of the ultrasonic sensor and the holding function of the jaw are integrated, taking the jaw in and out from the trocar does not become an obstacle, and the usability as a surgical instrument is not reduced.

At least one of the casing and the tissue pad may be mounted on the jaw main body by adhesion.

As described above, since the tissue pad is provided, it is possible to use a medical adhesive to adhere the casing or the tissue pad.

The jaw main body may have a recessed portion provided to at least one of a side of the casing and a side of the tissue pad, and at least one of the casing and the tissue pad may have a projecting portion engaging with the recessed portion.

It is also possible to mount the casing or the tissue pad on the jaw main body by the projecting portion engaging with the recessed portion provided to the jaw main body, without using a medical adhesive.

The jaw may include a jaw main body connected to the shaft, a thermal contraction tube that is mounted on the jaw main body and covers the phased array ultrasonic sensor therein, and a tissue pad mounted on an opposite side of the jaw main body from the thermal contraction tube.

With this configuration, since the phased array ultrasonic sensor is covered by the thermal contraction tube, the electronic material constituting the ultrasonic sensor is prevented from being exposed, and the biocompatibility of the jaw is maintained. Further, since the tissue pad is provided, the influence of friction and heat on the ultrasonic sensor is reduced.

At least one of the thermal contraction tube and the tissue pad may be mounted on the jaw main body by adhesion.

As described above, since the tissue pad is provided, it is possible to use a medical adhesive to adhere the thermal contraction tube or the tissue pad.

The jaw main body may have a side that is opposite to the shaft and divided into two or more ends, and the thermal contraction tube may cover the phased array ultrasonic sensor and one end of the jaw main body therein.

Since the thermal contraction tube covers the ultrasonic sensor and one end portion of the jaw main body therein, it is possible to fix the ultrasonic sensor to the jaw main body.

The jaw may include a jaw main body that is connected to the shaft and houses the phased array ultrasonic sensor, and a tissue pad mounted on the jaw main body.

With this configuration, since the phased array ultrasonic sensor is covered by the jaw main body, the electronic material constituting the ultrasonic sensor is prevented from being exposed, and the biocompatibility of the jaw is maintained. Further, since the tissue pad is provided, the influence of friction and heat on the ultrasonic sensor is reduced.

The jaw may include a jaw main body connected to the shaft, and tissue pad and casing that is mounted on the jaw main body and houses the phased array ultrasonic sensor, a part or all of the tissue pad and casing being formed of polyurethane.

With this configuration, since the jaw includes the tissue pad and casing formed of polyurethane, it is unnecessary to separately provide a tissue pad.

The jaw main body may be formed of a metal.

Since the jaw main body is connected to the shaft and is a portion driven when opening and closing the jaw, it is possible to secure strength by forming the jaw main body with a metal.

The tissue pad and casing includes a tissue pad portion formed of polyurethane, and a casing portion that is formed of a material different from polyurethane and houses the phased array ultrasonic sensor.

The tissue pad and casing may be formed of two kinds of materials. Such a structure can be realized by two-color molding.

The jaw may include a supporting member having a rigidity higher than that of the phased array ultrasonic sensor.

With this configuration, it is possible to secure the strength of the jaw by the supporting member.

Advantageous Effects of Invention

As described above, according to the present technology, it is possible to provide a handheld instrument for endoscope surgery having an ultrasonic imaging function with a practicable spatial resolution. It should be noted that the effect described here is not necessarily limitative and may be any effect described in the present disclosure.

MODE(S) FOR CARRYING OUT THE INVENTION

An instrument for endoscopic surgery according to this embodiment will be described.

[Configuration of Observation System]

Figure 1:
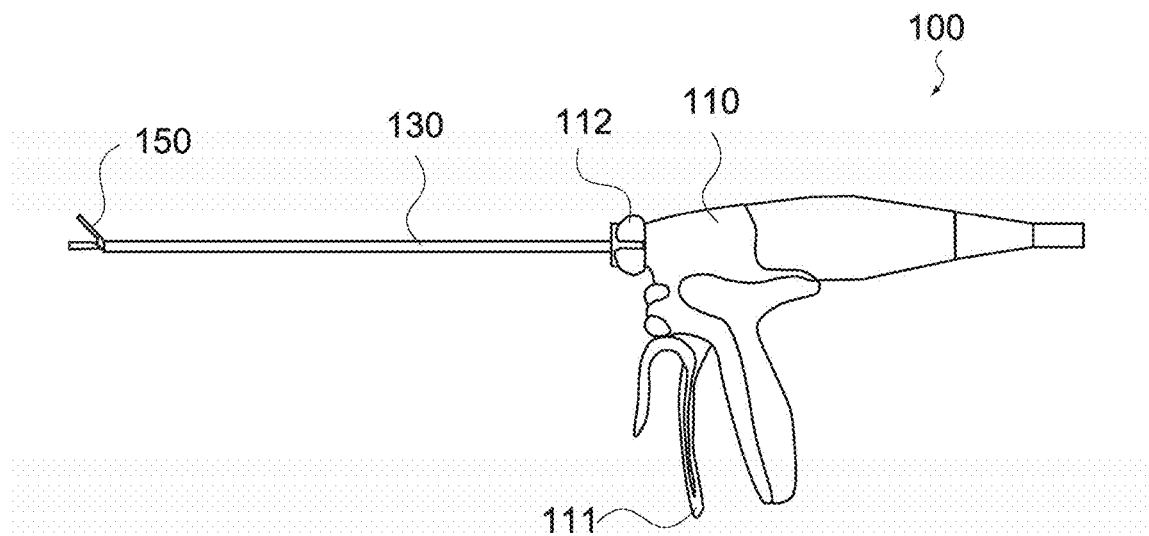
FIG. 1 is a plan view of a handheld instrument for endoscope surgery according to an embodiment of the present technology.

FIG. 1 is a plan view showing an entire configuration of a handheld instrument for endoscope surgery (hereinafter, referred to as handheld instrument) 100 according to this embodiment. The handheld instrument 100 is an ultrasonic coagulation/incision apparatus. However, this embodiment is applicable to a handheld instrument for endoscope surgery having a holding function, in addition to the ultrasonic coagulation/incision apparatus.

As shown in the figure, the handheld instrument 100 includes a handle 110, a shaft 130, and a jaw 150. The jaw 150 is provided at one end of the shaft 130. The handle 110 is provided at an end portion of the shaft 130 opposite to the jaw 150.

The jaw 150 is configured to be openable and closeable. When a practitioner operates a trigger 111 provided to the handle 110, the operation is transmitted to the jaw 150 via an operation transmission mechanism inserted through the shaft 130, and the jaw 150 is opened and closed.

Accordingly, it is possible to hold a biological tissue by the jaw 150. Further, when a practitioner rotates a rotation knob 112 provided to the handle 110, the shaft 130 connected to the rotation knob 112 is rotated, and the rotation angle of the jaw 150 with respect to the handle 110 is adjusted.

The jaw 150 may be one capable of cutting a biological tissue as well as holding the biological tissue. Although the jaw 150 is configured to be capable of cutting the held biological tissue by ultrasonic waves in the following description, the jaw 150 may have only a holding function. Examples of the handheld instrument for surgery having a holding function include forceps, a bipolar hemostasis apparatus having an incision function, and an automatic suturing apparatus. This embodiment is applicable to any of these instruments.

[Configuration of Jaw]

Figure 2:
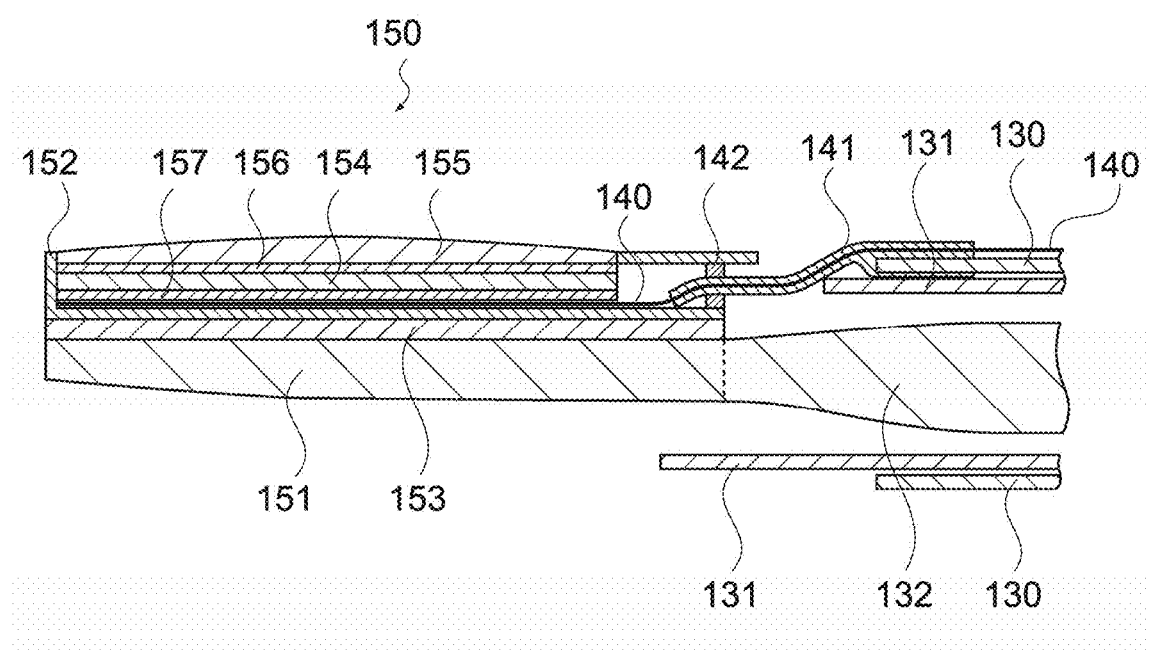
FIG. 2 is a cross-sectional view showing a configuration of a jaw provided in the handheld instrument for endoscope surgery.
Figure 3:
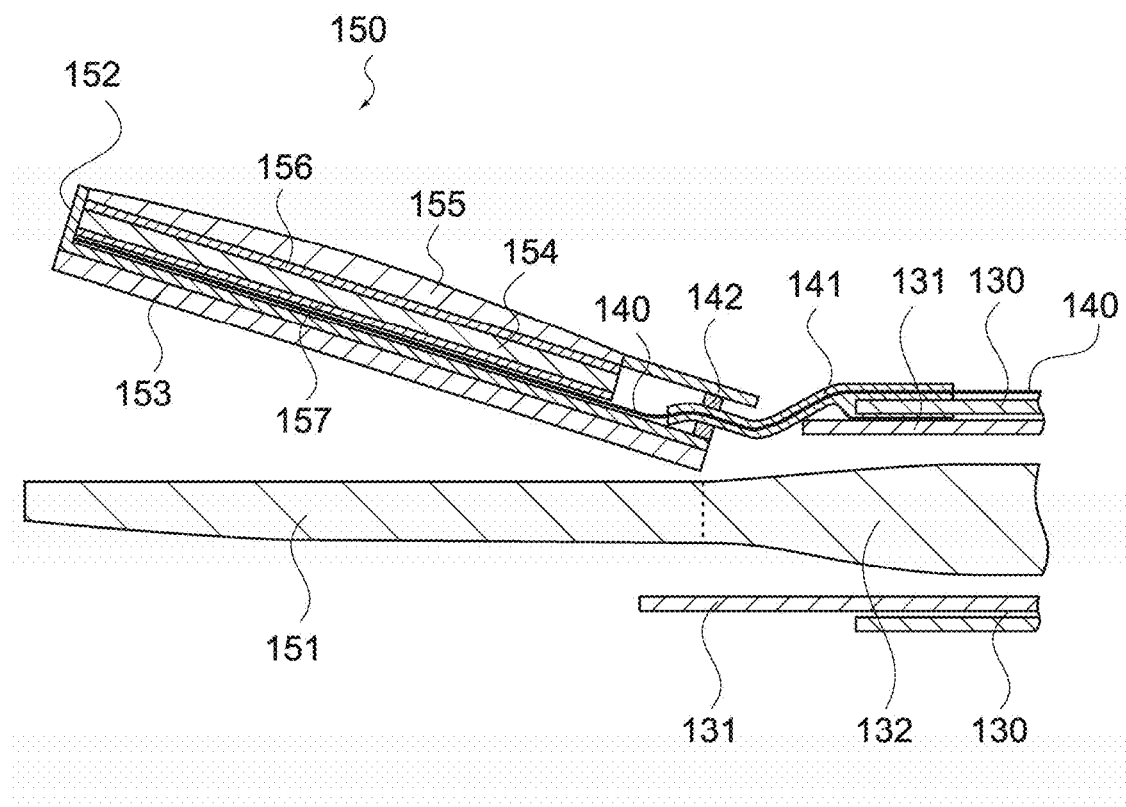
FIG. 3 is a cross-sectional view showing the configuration of the jaw provided in the handheld instrument for endoscope surgery.

A detailed configuration of the jaw 150 will be described. FIG. 2 and FIG. 3 are each a partial cross-sectional view of the jaw 150 and the shaft 130.

The jaw 150 shown in these figures includes a probe 151 and a movable jaw 152.

The probe 151 is connected to an ultrasonic transmission rod 132 inserted through the shaft 130, and receives ultrasonic waves transmitted from the ultrasonic transmission rod 132 to vibrate. In this way, the probe 151 functions as a blade for ultrasonic coagulation incision.

The movable jaw 152 is connected to a jaw driving pipe 131 inserted through the shaft 130, and configured to be openable and closable with respect to the probe 151 as shown in FIG. 2 and FIG. 3 when the jaw driving pipe 131 moves back and forth along the extending direction of the shaft 130. Accordingly, it is possible to hold a biological tissue by the movable jaw 152 and the probe 151.

The movable jaw 152 includes a tissue pad 153, an ultrasonic transducer array 154, an acoustic lens 155, an acoustic matching layer 156, and a backing layer 157.

The tissue pad 153 is placed on the probe 151 in the movable jaw 152, and holds a biological tissue together with the probe 151 when the movable jaw 152 is closed.

Figure 4:
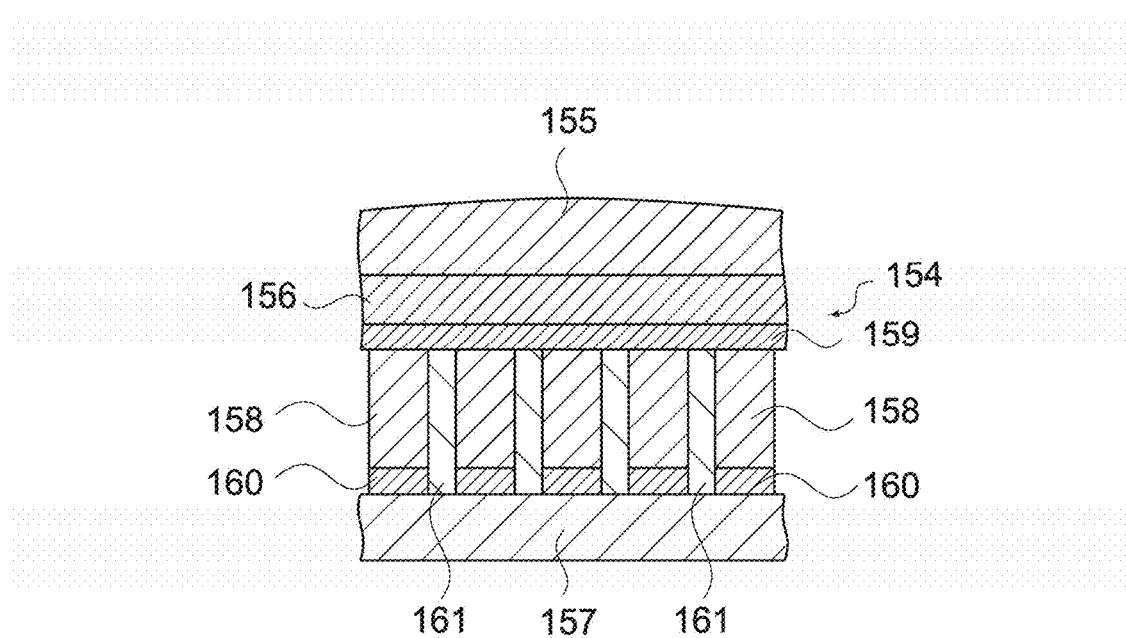
FIG. 4 is a cross-sectional view showing a configuration of an ultrasonic transducer array mounted on the jaw provided in the handheld instrument for endoscope surgery.

FIG. 4 is a schematic diagram showing a configuration of the ultrasonic transducer array 154. As shown in the figure, the ultrasonic transducer array 154 includes ultrasonic transducers 158, an upper electrode 159, and a lower electrode 160.

The ultrasonic transducers 158 are each formed of a piezoelectric material such as PZT (lead titanate zirconate), and a plurality of ultrasonic transducers 158 are arranged to constitute a phased array. Between the ultrasonic transducers 158, a filler 161 such as an acoustic absorber formed of epoxy resin or the like is filled.

The upper electrode 159 and the lower electrode 160 are each formed of a conductive material, and arranged so as to sandwich the ultrasonic transducers 158. The lower electrode 160 is separated for each of the ultrasonic transducers 158, and the upper electrode 159 is formed over the plurality of ultrasonic transducers 158.

The upper electrode 159 and the lower electrode 160 are each connected to a signal wiring 140. When voltage is applied between the upper electrode 159 and the lower electrode 160, vibration caused by the inverse piezoelectric effect occurs in the ultrasonic transducers 158 to generate ultrasonic waves. Further, when the reflected wave enters the ultrasonic transducers 158, polarization due to the piezoelectric effect occurs, and is output via the signal wiring 140.

The configuration of the ultrasonic transducer array is not limited to that shown here as long as the plurality of ultrasonic transducers 158 constitute a phased array. The size of each of the ultrasonic transducers 158 is not particularly limited, and may be, for example, 250 µm square. The number of ultrasonic transducers 158 constituting the ultrasonic transducer array 154 may be several tens to several thousands.

The acoustic lens 155 focuses the ultrasonic waves generated by the ultrasonic transducers 158. The acoustic lens 155 is placed on the side opposite to the tissue pad 153 in the movable jaw 152, and brought into contact with a biological tissue to be observed. The acoustic lens 155 is formed of nylon resin or the like such as silicone rubber and polyether amide copolymer, and the size or shape thereof is not particularly limited. As will be described later, the acoustic lens 155 is preferably formed of a material having an acoustic impedance of not less than 1.35 M rayls and not more than 1.74 M rayls.

The acoustic matching layer 156 reduces the difference in acoustic impedance between the biological tissue and the ultrasonic transducers 158, and prevents ultrasonic waves from being reflected toward the biological tissue. The acoustic matching layer 156 is formed of synthetic resin or a ceramic material. The acoustic matching layer 156 may have a plurality of layers.

The backing layer 157 is placed between the ultrasonic transducer array 154 and the tissue pad 153, and absorbs unnecessary vibration of the ultrasonic transducers 158. The backing layer 157 is formed of a material obtained by mixing a filler and synthetic resin, or the like. As will be described later, the backing layer 157 is preferably formed of a material having an acoustic impedance of not more than 2.05 M rayls and an acoustic attenuation constant of not less than 2.29 dB/MHz/mm.

The jaw 150 has the configuration described above. By sandwiching a biological tissue by the movable jaw 152 and the probe 151 and applying ultrasonic waves from the probe 151, it is possible to coagulate or incise the sandwiched biological tissue.

Further, by applying ultrasonic waves emitted from the movable jaw 152 to the biological tissue in contact with the acoustic lens 155 and detecting the reflected wave, it is possible to generate an ultrasonic image. That is, on the movable jaw 152, an ultrasonic sensor capable of performing the ultrasonic imaging is mounted.

Figure 18:
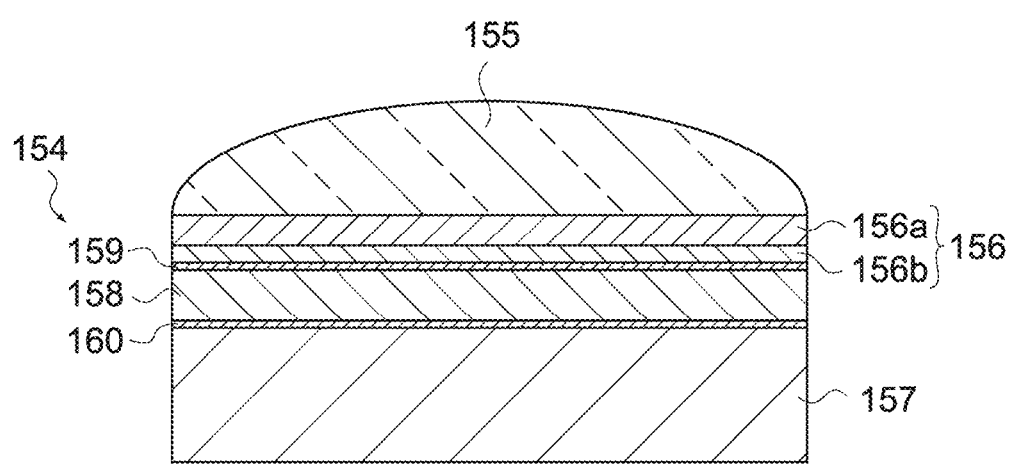
FIG. 18 is a cross-sectional view showing a configuration of an ultrasonic sensor mounted on the jaw provided in the handheld instrument for endoscope surgery according to the embodiment of the present technology.
Figure 19:
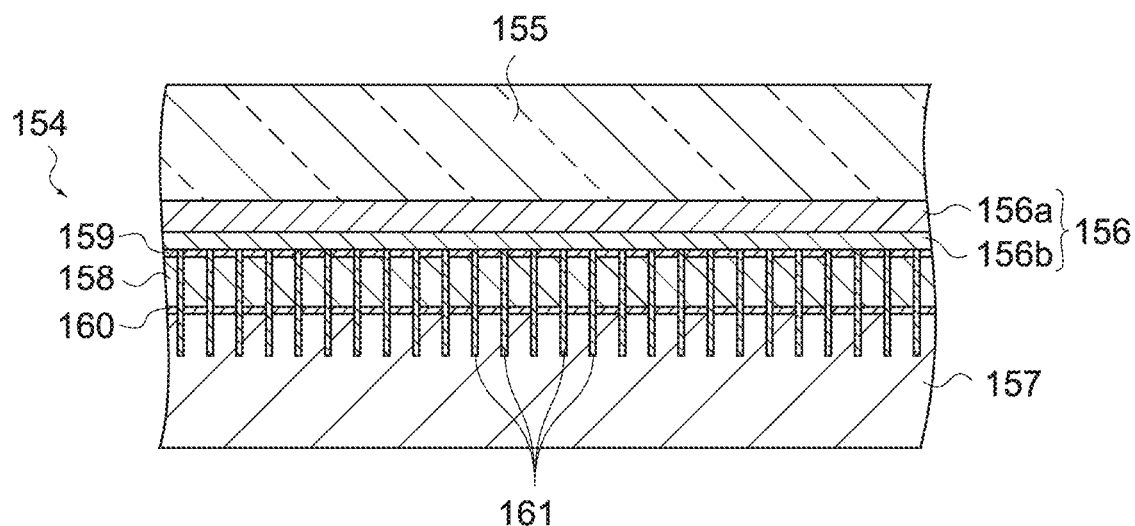
FIG. 19 is a cross-sectional view showing the configuration of the ultrasonic sensor mounted on the jaw provided in the handheld instrument for endoscope surgery.

A phased array ultrasonic sensor to be mounted on the handheld instrument 100 according to this embodiment is preferably one having a structure capable of reducing the height. FIG. 18 and FIG. 19 are each a cross-sectional view of a phased array ultrasonic sensor having a reduced height applicable to this embodiment. FIG. 18 is a cross-sectional view taken along the plane perpendicular to the extending direction of the shaft 130, and FIG. 19 is a cross-sectional view as seen from the same direction as that in FIG. 2.

As described above, the phased array ultrasonic sensor includes the ultrasonic transducer array 154, the acoustic lens 155, the acoustic matching layer 156, and the backing layer 157. The ultrasonic transducer array 154 includes the ultrasonic transducers 158, the upper electrode 159, and the lower electrode 160, and the acoustic matching layer 156 includes a first acoustic matching layer 156a and a second acoustic matching layer 156b.

The acoustic lens 155 is preferably formed of a material having an acoustic impedance of not less than 1.35 M rayls and not more than 1.74 M rayls. Further, the backing layer 157 is preferably formed of a material having an acoustic impedance of not more than 2.05 M rayl, and is more preferably formed of a material having an acoustic impedance of not more than 2.05 M rayl and an acoustic attenuation constant of not less than 2.29 dB/MHz/mm.

The thickness of the phased array ultrasonic sensor will be discussed below. Favorable examples of a small-sized phased array ultrasonic sensor include an ultrasonic sensor of an intracardiac ultrasonic catheter. Since it has a footprint of 2×10 mm while including a transducer element of not less than 64 ch, the size thereof is close to that of the phased array ultrasonic sensor to be mounted on the movable jaw 152 as in this embodiment.

However, in the ultrasonic sensor of an intracardiac ultrasonic catheter, the thickness from the acoustic lens to the backing layer is approximately 2.3 mm. Therefore, in the case of mounting this ultrasonic sensor on the movable jaw 152 as it is, the diameter at the tip exceeds 5 mm. As a result, it gets caught when being taken in and out from a trocar, and the operability of the handheld instrument 100 is significantly reduced.

Since also a general handheld instrument for endoscope surgery needs the thickness of the tissue pad and jaw structure of 2.0 mm, the thickness from the tissue pad 153 to the acoustic lens 155 needs to be reduced to not more than 2.0 mm also in the handheld instrument 100 according to this embodiment.

Examples of means for reducing the height include thinning of the acoustic lens 155 and the backing layer 157. The thickness of the acoustic lens 155 can be reduced by forming the acoustic lens 155 of a material having an acoustic impedance similar to that (not less than 1.35 M rayls and not more than 1.74 M rayls although different depending on the part) of a living body to be brought into contact with the acoustic lens 155 (Reference 1: Ben Cox, "Acoustics for Ultrasound Imaging", University College of London Lecturenotes (2013), retrieved from https://www.ucl.ac.uk/medphys/staff/people/bcox/USlecturenotes_Jan2013.pdf.).

Examples of the material having an acoustic impedance of not less than 1.35 M rayls and not more than 1.74 M rayls include a nylon polymer, an aromatic polymer, aliphatic polymer, and acrylic resin. Note that in order to adjust the acoustic focusing/acoustic impedance, a filler may be mixed with the above-mentioned materials to form a composite. Examples of the filler include other types of polymer materials such as acrylic, polyurethane, silicone, and rubber polymer materials, inorganic oxides such as $TiO_x$, $AlO_x$, $ZnO_x$, $SiO_x$, and $HfO_x$ (x is adjusted to the preferred composition), and metal powder such as W, Pt, Ag, and Au powders.

In the configuration shown in FIG. 18 and FIG. 19, by forming the acoustic lens 155 of a material having an acoustic impedance of 1.52 M rayls, the thickness of the acoustic lens 155 can be reduced to 0.3 mm.

A material having a low acoustic impedance and a high acoustic absorption performance is used for the backing layer 157. Accordingly, the backing layer 157 has a structure of reflecting most of ultrasonic waves toward the back surface direction (opposite direction to the acoustic lens 155) and efficiently absorbing slight sound waves that has passed therethrough.

First, an acoustic impedance will be discussed. When forming the backing layer 157 of a material having a low acoustic impedance, a reverberation component is generated. The reverberation component adversely affects the derivation of a dead zone where the region in the vicinity of the transducer cannot be observed due to the dead time, and the increase in distance resolution. According to a reference 2 (M. G. Mooney et al., "Linear Array Transducers with Improved Image Quality for Vascular Ultrasonic Imaging", Hewlett-Pachard Journal August (1994), p. 43-51), the distance resolution is specified by −20 dB, and the distance resolution is increased.

In the case of reducing the height of the ultrasonic sensor, the thickness available for the backing layer is only not more than 1 mm, and the acoustic absorption performance is insufficient particularly at low frequencies. In this regard, in general, a method of adding a dematching layer, reflecting sound waves directed to the back surface, and absorbing the remaining waves by the backing layer is adopted. However, adding a dematching layer increases the total thickness and the number of production steps, which increases the cost.

Meanwhile, in this embodiment, a material that acoustically mismatches the backing layer 157 is selected. According to the reference 2, since the distance resolution is specified by −20 dB width, it is configured to reflect 90% or more of the generated sound waves.

Specifically, when the acoustic impedance of the ultrasonic transducers 158 is represented by $z_2$ and the acoustic impedance of the backing layer 157 is represented by $z_1$, a reflectance $\tau_p$ is represented by the following (equation 1).

[Math. 1]

$$\tau_p = \frac{z_2 - z_1}{z_2 + z_1} \quad \text{(Equation 1)}$$

Note that although the piezoelectric material used for medical applications is a single crystal material such as PZT and PMNPT, the acoustic impedance thereof is not more than 29 to 37 M rayls. This acoustic impedance is used as $z_1$ to calculate $z_2$ that gives the reflectance $\tau_p$ of not less than 90%, thereby obtaining $z_2$ of not more than 2.05 to 1.52 M rayls. Therefore, the backing layer 157 is preferably formed of a material having an acoustic impedance of not more than 2.05 M rayl.

Next, the acoustic absorption performance will be discussed. By forming the backing layer 157 of a material having a high acoustic absorption performance, it is possible to thin the backing layer 157. For example, while a general backing material obtained by mixing W powder with acrylic resin has an acoustic attenuation constant of approximately 1.40 dB/MHz/mm, the acoustic attenuation constant of a high acoustic absorption material reaches 2.29 to 5.0 dB/MHz/mm, so that the backing layer 157 is expected to be thinned.

Meanwhile, the reverberation component of not more than −20 dB width generated by forming the backing layer 157 of a material having a low acoustic impedance increases ring-down artifact that is a virtual image created by reverberation) and background noise, which causes poor contrast, it needs to be suppressed. Therefore, there is a need to suppress the reverberation component.

In the handheld instrument 100, since it aims to observe a target object at a depth where an operator cannot view the target object, such a depth is set to at least not less than 3 mm (reference 3:V. Tuchin; Tissue Optics: Light Scattering Methods and Instruments for Medical Diagnosis. SPIE Press) and the reverberation noise component at 7 MHz is set to not more than −60 dB on the basis of transmitted ultrasonic maximum intensity. As a result, the backing layer 157 needs to be formed of a material having an acoustic attenuation constant of not less than 2.29 dB/MHz/mm.

From the above, the backing layer 157 is preferably formed of a material having an acoustic impedance of not more than 2.05 M rayl, and is more preferably formed of a material having an acoustic impedance of not more than 2.05 M rayl and an acoustic attenuation constant of not less than 2.29 dB/MHz/mm. Examples of the material having an acoustic impedance of not more than 2.05 M rayl and an acoustic attenuation constant of not less than 2.29 dB/MHz/mm include polyurethane such as expandable polyurethane.

In the configuration shown in FIG. 18 and FIG. 19, by forming the backing layer 157 of a material having an acoustic impedance of 2.05 M rayl and an acoustic attenuation constant of 2.29 dB/MHz/mm, it is possible to reduce the thickness of the backing layer 157 to not more than 0.4 mm while suppressing reverberation.

With the structure of the acoustic lens 155 and the backing layer 157 as described above, it is possible to reduce the thickness from the acoustic lens 155 to the backing layer 157 to 0.94 mm in the configuration shown in FIG. 18 and FIG. 19. Accordingly, it is possible to prevent the handheld instrument 100 from getting caught when being taken in and out from the trocar.

A specific example of improvement in thickness will be described. A case where as a material constituting the backing layer (hereinafter, referred to as backing material), a backing material A or a backing material B is used when the acoustic impedance of a piezoelectric material constituting an ultrasonic transducer is 29 M rayls will be discussed.

The backing material A is obtained by adding a filler to a general epoxy material, and has an acoustic impedance of 8.7 M rayls and an acoustic attenuation constant of 3.00 dB/MHz/mm. The backing material B is expandable polyurethane, and has an acoustic impedance of 1.57 M rayls and an acoustic attenuation constant of 2.29 dB/MHz/mm.

Calculating the reflectance according to the above-mentioned (equation 1) results in 55.4% for the backing material A and 90.5% for the backing material B. At this point, the intensity of sound waves toward the back surface direction, which become reverberation later, has already reduced to approximately ⅕.

Figure 20:
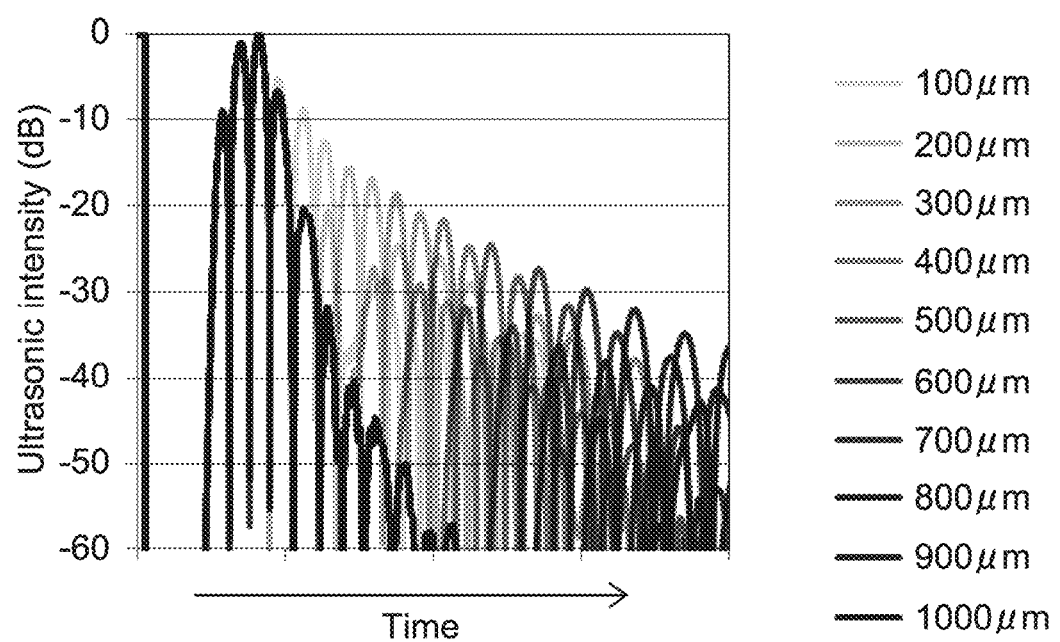
FIG. 20 is a simulation result showing the influence on acoustic absorption performance by the thickness of a backing layer.
Figure 21:
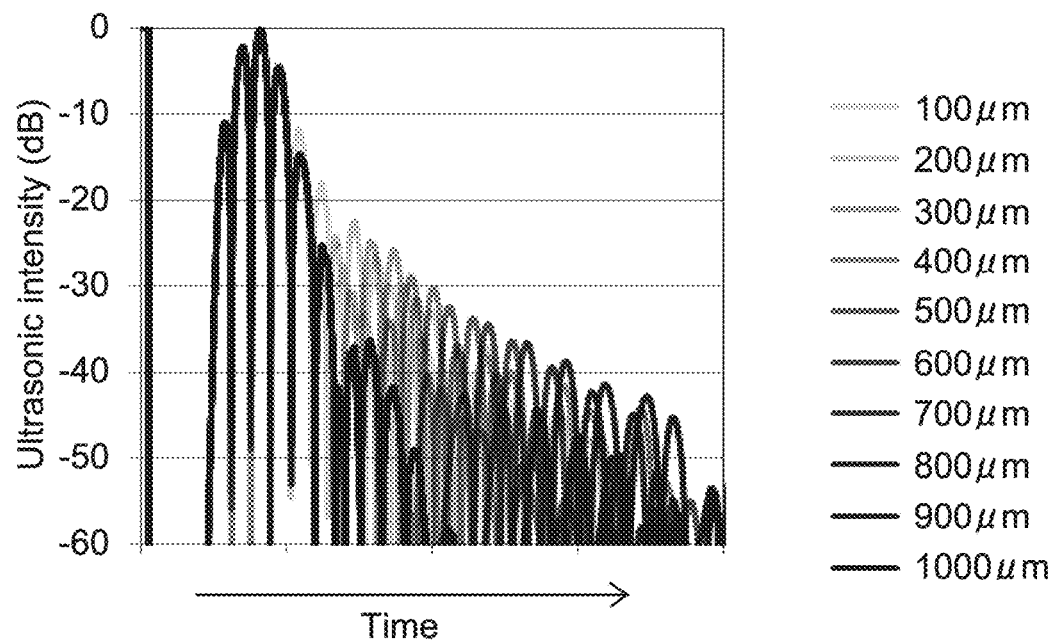
FIG. 21 is a simulation result showing the influence on acoustic absorption performance by the thickness of the backing layer.

Next, acoustic absorption is performed by the backing layer. In order to compare the acoustic absorption performance regardless of the device structure, the thickness of the backing layer is simulated by being changed in the range of 100 to 1000 μm, and the waveform is converted into absolute values. FIG. 20 is a simulation result of the backing material A, and FIG. 21 is a simulation result of the backing material B.

As shown in the figures, the backing material A (FIG. 20) has greater acoustic absorption performance. However, because of the reduction in sound waves toward the back surface direction, the backing material B (FIG. 21) has faster sound attenuation. When evaluating (converting into a distance width by sound speed×time width) the 20 dB width and 60 dB width with an envelope made by data of each layer thickness, it is 1.1 mm for the backing material A and 0.4 mm for the backing material B in the case of −20 dB width. Further, in the case of −60 dB width, it is 4.7 mm for the backing material A and 3.3 mm for the backing material B.

As described above, the backing material B is superior in both of −20 dB width showing the distance resolution or −60 dB representing dead zone. Therefore, the backing layer 157 is preferably formed of a material having an acoustic attenuation constant of not less than 2.29 dB/MHz/mm.

[Regarding Signal Wiring]

To the ultrasonic transducer array 154, as described above, the signal wiring 140 is connected. Since the signal wiring 140 includes a large number of signal wirings to be connected to the ultrasonic transducers 158 constituting the ultrasonic transducer array 154, the signal wiring 140 may be a flexible printed circuit board.

As shown in FIG. 2, a part of the signal wiring 140 over the movable jaw 152 and the shaft 130 is covered by a covering member 141. The covering member 141 is formed of a waterproof coating material such as polymer coating material and a rubber material, and deformed according to the opening and closing of the movable jaw 152 to protect the signal wiring 140 from contact with liquid such as blood, another surgical instrument, and the like and suppress disconnection of the signal wiring 140.

Further, a sealing member 142 is placed on a portion of the signal wiring 140 led out from the movable jaw 152. The sealing member 142 is a waterproof cap formed of synthetic resin, a rubber material, or the like. An opening is provided in the sealing member 142, and the signal wiring 140 and the covering member 141 are inserted therethrough. The portion of the signal wiring 140 led out from the movable jaw 152 is sealed by the sealing member 142, thereby preventing liquid from entering the movable jaw 152.

Figure 5:
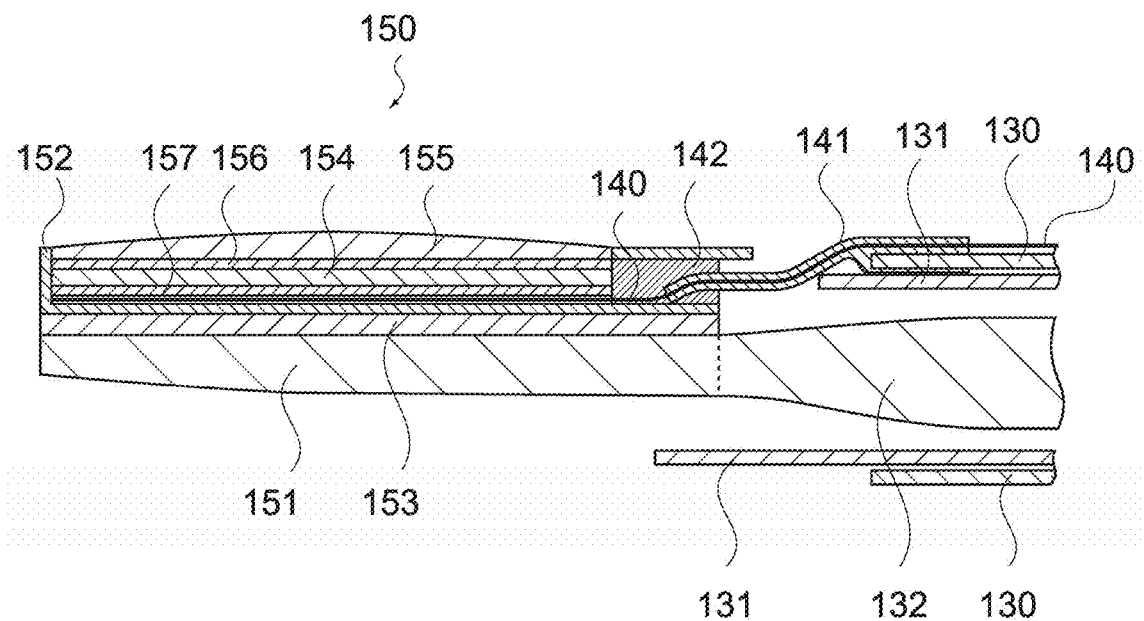
FIG. 5 is a cross-sectional view showing the configuration of the jaw provided in the handheld instrument for endoscope surgery.
Figure 6:
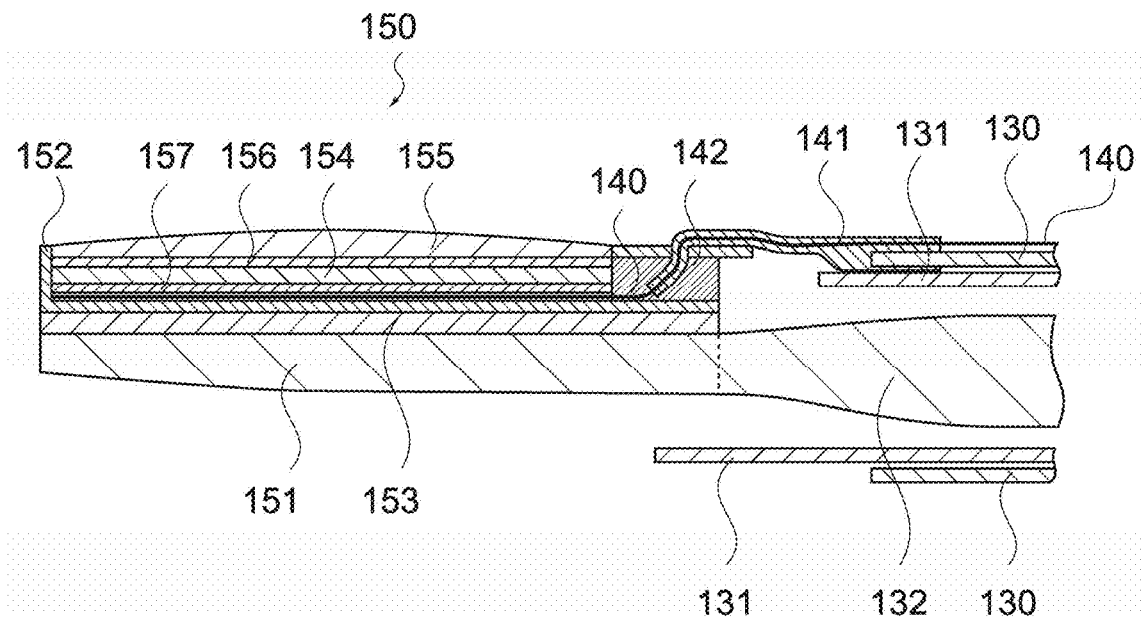
FIG. 6 is a cross-sectional view showing the configuration of the jaw provided in the handheld instrument for endoscope surgery.

FIG. 5 and FIG. 6 are each a schematic diagram showing another configuration of the sealing member 142. As shown in FIG. 5, the sealing member 142 may seal the entire portion of the signal wiring 140 led out from the movable jaw 152. With this configuration, it is possible to further improve the waterproofness by the sealing member 142.

Further, as shown in FIG. 6, the signal wiring 140 may be introduced from above the movable jaw 152. Accordingly, it is possible to prevent the signal wiring 140 from being damaged by being brought into contact with the ultrasonic transmission rod 132 and the probe 151 that emit ultrasonic vibration. Further, since the clearance between the movable jaw 152 and the ultrasonic transmission rod 132 is widened, dregs such as the coagulated blood and a biological tissue are unlikely to be accumulated, and easily removed.

[Regarding Shaft]

Figure 7:
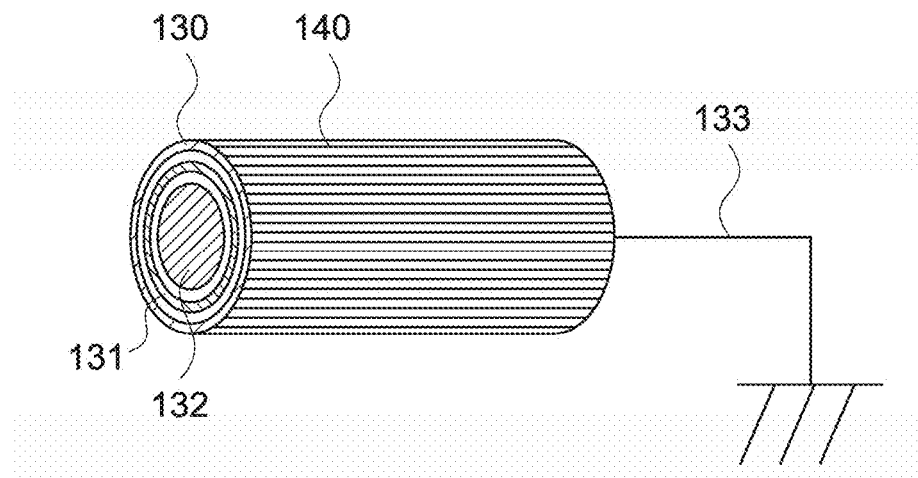
FIG. 7 is a schematic diagram showing a configuration of a shaft provided in the handheld instrument for endoscope surgery.

FIG. 7 is a schematic diagram showing a configuration of the shaft 130. As shown in the figure, the tubular jaw driving pipe 131 is inserted through the shaft 130, and the ultrasonic transmission rod 132 is inserted through the jaw driving pipe 131.

The shaft 130 is a tubular member formed of metal, and connects the handle 110 and the jaw 150. The shaft 130 is fixed to the rotation knob 112, is rotated with the rotation of the rotation knob 112, and rotates the jaw 150 with respect to the handle 110.

The jaw driving pipe 131 is connected to the trigger 111 provided to the handle 110, and moves back and forth along the extending direction of the shaft 130 when the trigger 111 is operated, thereby to open and close the jaw 150. Further, the handheld instrument 100 may include an operation transmission mechanism that is provided in the shaft 130 and transmits the operation of the trigger 111 to the jaw 150, in addition to the jaw driving pipe 131.

The ultrasonic transmission rod 132 is connected to an ultrasonic transmission mechanism (to be described later) provided to the handle 110, and transmits ultrasonic waves to the probe 151. The ultrasonic transmission rod 132 receives ultrasonic vibration generated by an ultrasonic generator connected to the ultrasonic transmission mechanism to vibrate. Thus, the ultrasonic transmission rod 132 is capable of transmitting ultrasonic waves to the probe 151.

On the outer peripheral surface of the shaft 130, the signal wiring 140 that is a flexible printed circuit board is placed. Since the jaw driving pipe 131 and the ultrasonic transmission rod 132 are inserted through the shaft 130, it is difficult to pass the signal wiring 140 through the shaft 130. However, by placing the signal wiring 140 on the outer peripheral surface of the shaft 130, it is possible to pass the signal wiring 140 from the jaw 150 to the handle 110.

This is not limited to the case where the handheld instrument 100 has an ultrasonic coagulation/incision function as described above. Also in the case where the handheld instrument 100 is forceps, a bipolar hemostasis apparatus having an incision function, an automatic suturing apparatus, or the like, since there is some mechanism inside the shaft 130, it is effective to place the signal wiring 140 on the outer peripheral surface of the shaft 130.

Further, as shown in FIG. 7, the shaft 130 is connected to the ground potential by a ground wiring 133, i.e., the shaft 130 is electrically fixed at ground potential. By electrically fixing the shaft 130 at ground potential, it is possible to prevent from noise in the signal wiring 140 from occurring.

Figure 8:
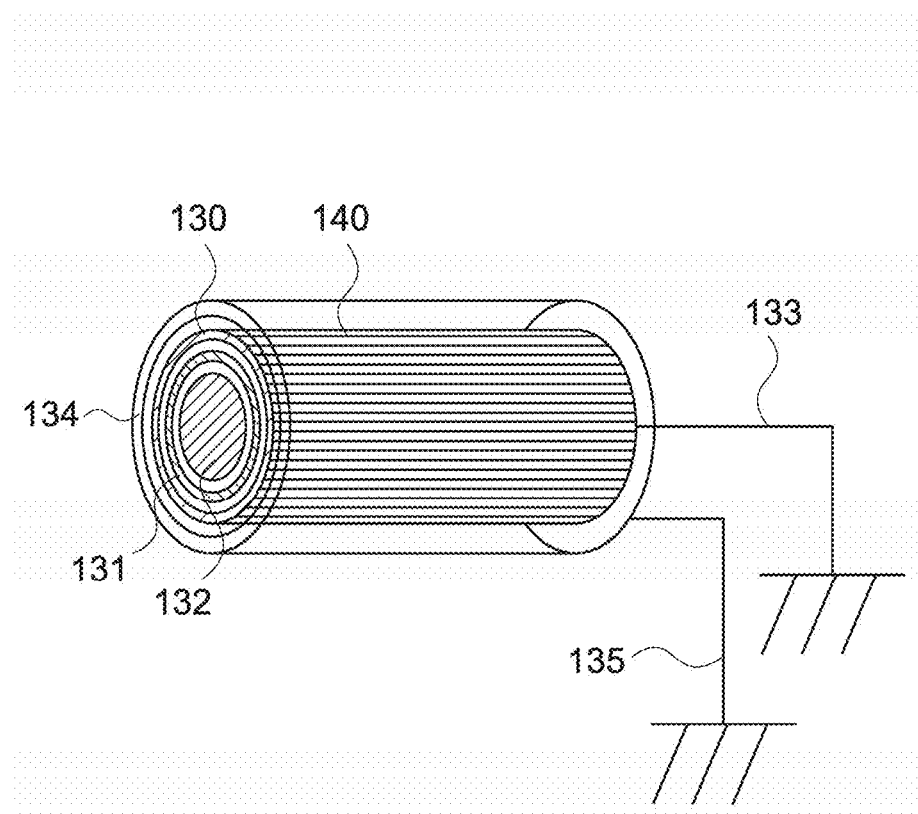
FIG. 8 is a schematic diagram showing a configuration of the shaft provided in the handheld instrument for endoscope surgery.
Figure 9:
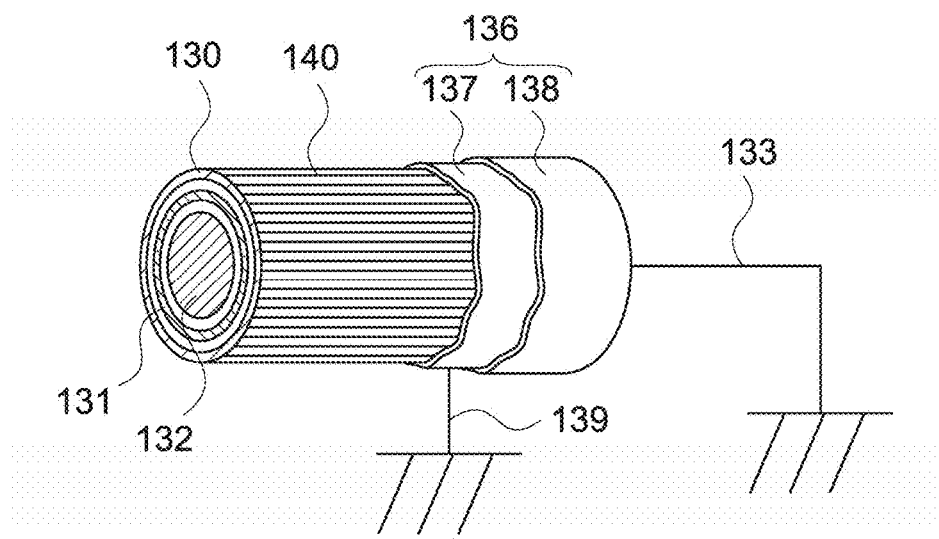
FIG. 9 is a schematic diagram showing the configuration of the shaft provided in the handheld instrument for endoscope surgery.

FIG. 8 and FIG. 9 are each a schematic diagram showing another configuration of the shaft 130. As shown in FIG. 8, the handheld instrument 100 may include a protective member 134. The protective member 134 is a tubular member formed of metal, and the shaft 130 is inserted therethrough. Accordingly, the signal wiring 140 is covered by the protective member 134.

As shown in FIG. 8, the protective member 134 is connected to the ground potential by a ground wiring 135, i.e., the protective member 134 is electrically fixed at ground potential. Accordingly, the signal wiring 140 is sandwiched by the shaft 130 and the protective member 134 that are electrically fixed at ground potential, which makes it possible to more effectively prevent from noise in the signal wiring 140 from occurring. Further, the protective member 134 protects the signal wiring 140, and is capable of preventing the signal wiring 140 from being damaged by collision with another surgical instrument, or the like.

Further, as shown in FIG. 9, the handheld instrument 100 may include a protective member 136. The protective member 136 includes a metal layer 137 that covers the signal wiring 140, and a protective layer 138 that covers the metal layer 137.

The metal layer 137 may be a metal thin film formed on the signal wiring 140 by a deposition process, or a flexible printed circuit board having a solid pattern, or the like. The protective layer 138 may be formed by coating a polymer, glass coating, amorphous silicon, diamond-like carbon, or the like on the metal layer 137.

As shown in FIG. 9, the metal layer 137 is connected to the ground potential by a ground wiring 139, i.e., the metal layer 137 is electrically fixed at ground potential. Accordingly, the signal wiring 140 is sandwiched by the shaft 130 and the metal layer 137 that are electrically fixed at ground potential, which makes it possible to prevent from noise in the signal wiring 140 from occurring. Further, the protective layer 138 prevents the signal wiring 140 from being damaged. Note that the protective member 136 may include only any of the metal layer 137 and the protective layer 138.

[Regarding Rotation Knob]

Figure 10:
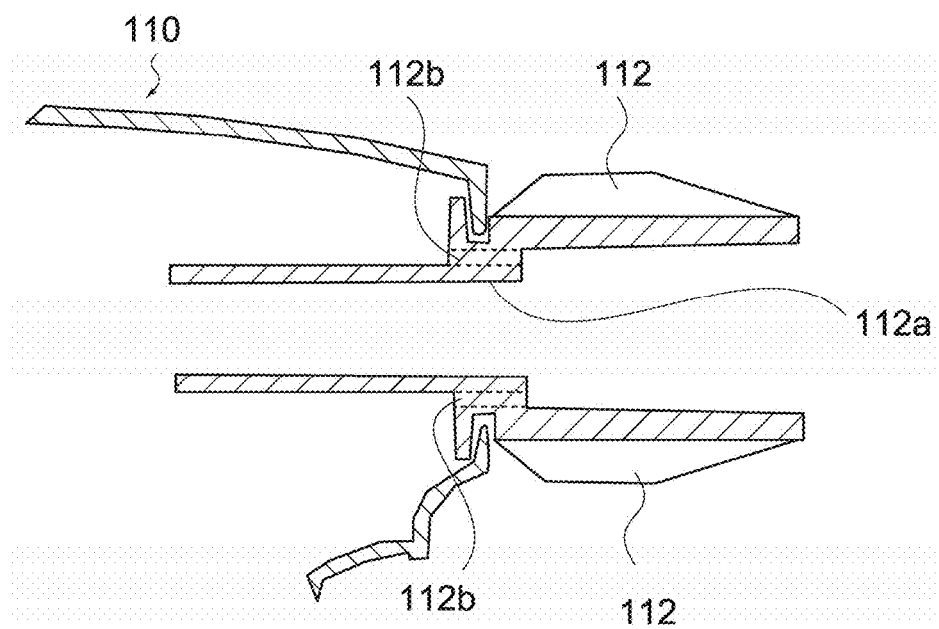
FIG. 10 is a cross-sectional view showing a configuration of a rotation knob provide in the handheld instrument for endoscope surgery.
Figure 11:
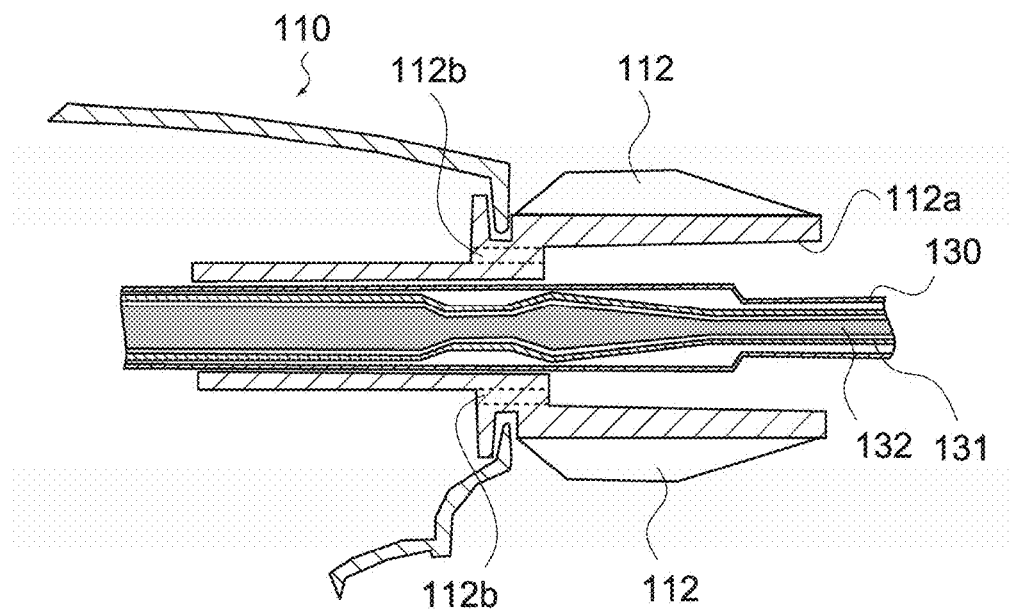
FIG. 11 is a cross-sectional view showing a configuration of the rotation knob provided in the handheld instrument for endoscope surgery.
Figure 12:
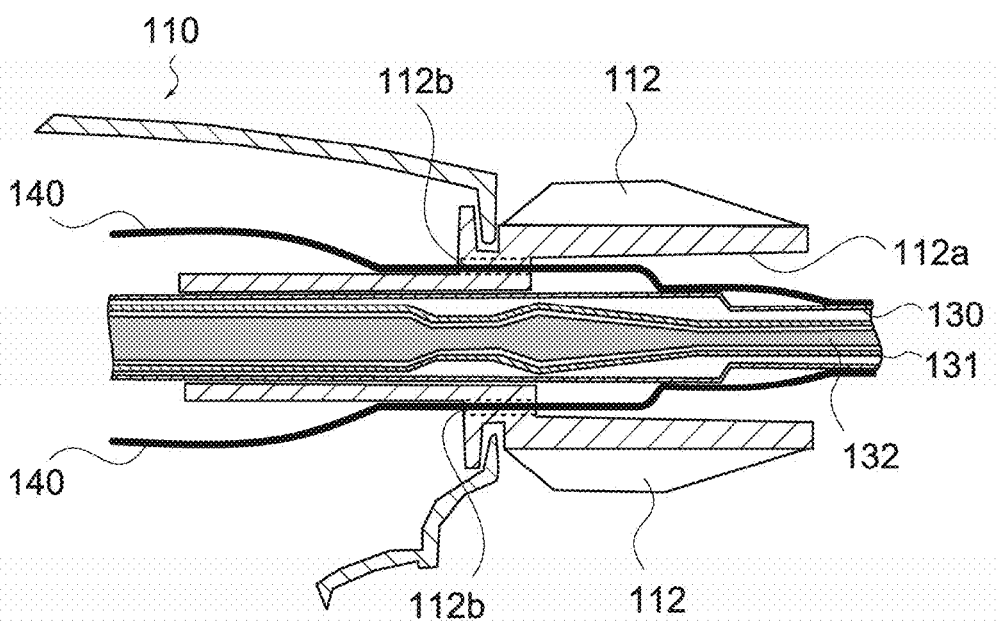
FIG. 12 is a cross-sectional view showing the configuration of the rotation knob provided in the handheld instrument for endoscope surgery.
Figure 13:
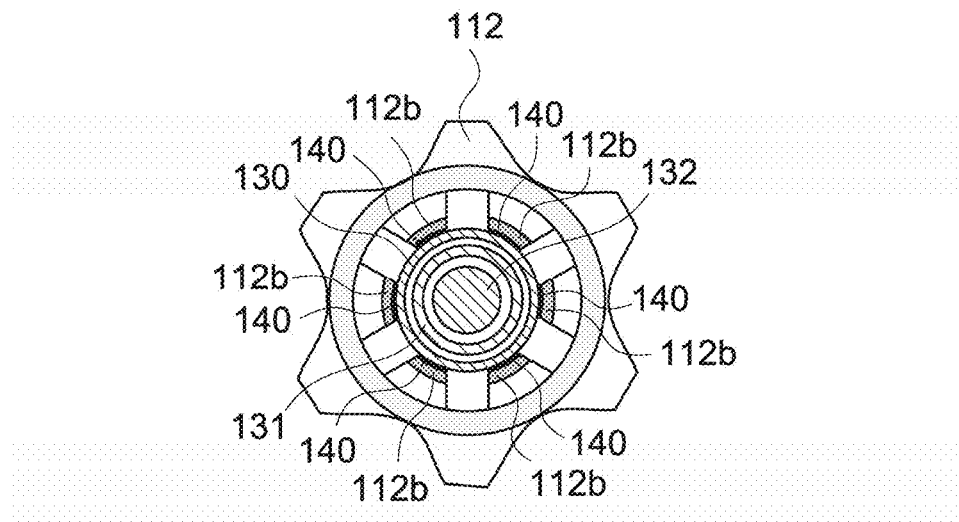
FIG. 13 is a plan view showing the configuration of the rotation knob provided in the handheld instrument for endoscope surgery.

As shown in FIG. 1, the rotation knob 112 is provided to the handle 110. FIG. 10 to FIG. 12 are each a cross-sectional view showing a configuration of the rotation knob 112, and FIG. 13 is a plan view showing the configuration of the rotation knob 112. As shown in FIG. 10, the rotation knob 112 is rotatably supported by the casing of the handle 110, and the through-hole 112a is provided around the rotation axis thereof.

As shown in FIG. 11, the ultrasonic transmission rod 132, the jaw driving pipe 131, and the shaft 130 are inserted through the through-hole 112a. The shaft 130 is fixed to the rotation knob 112. When the rotation knob 112 is rotated with respect to the handle 110, the shaft 130 is rotated with the rotation knob 112.

Note that as shown in FIG. 11 and FIG. 13, an introduction hole 112b is provided to the rotation knob 112. The introduction hole 112b is communicated with the inside of the casing of the handle 110 and the through-hole 112a, at the outer periphery of the jaw driving pipe 131.

As shown in FIG. 12 and FIG. 13, the signal wiring 140 is inserted through the introduction hole 112b, and introduced from the shaft 130 into the casing of the handle 110.

Figure 14:
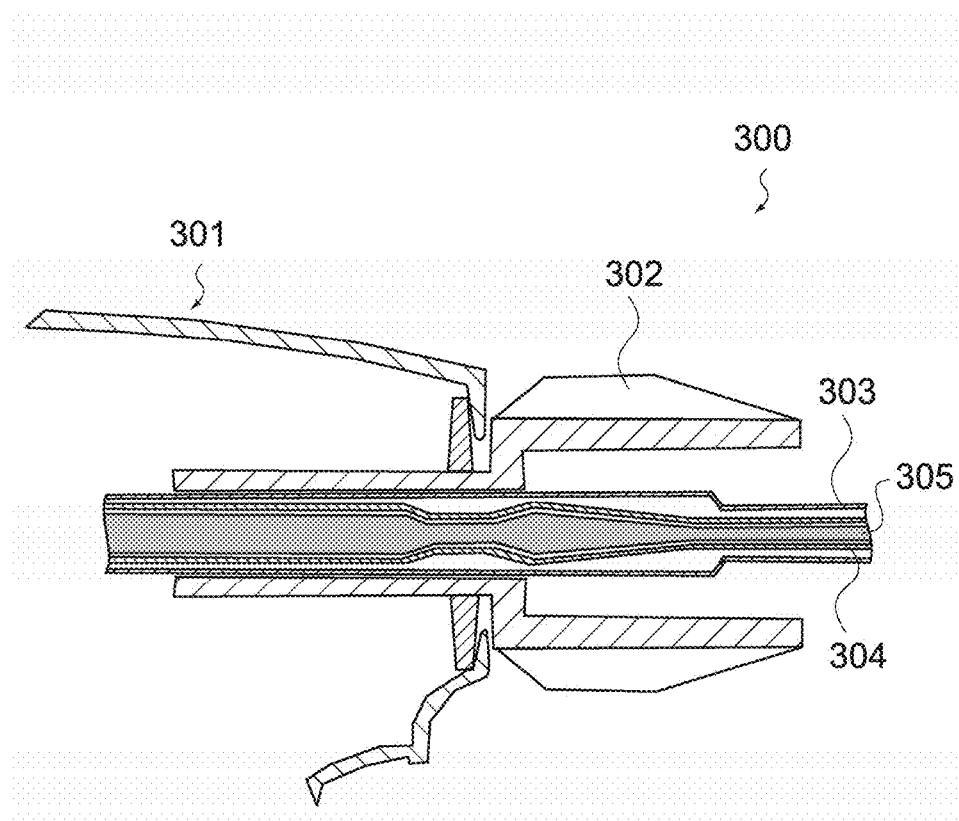
FIG. 14 is a cross-sectional view showing the configuration of a rotation knob provided in an existing handheld instrument for endoscope surgery.
Figure 15:
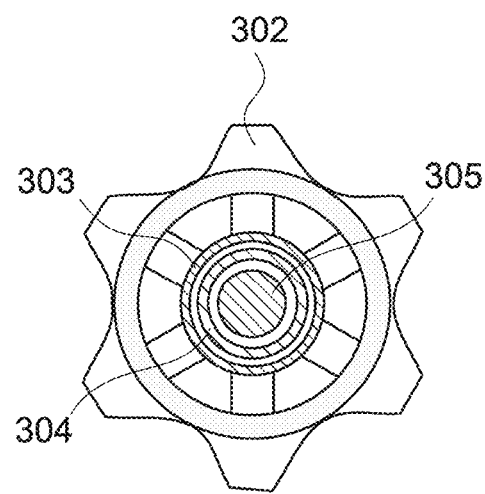
FIG. 15 is a cross-sectional view showing the configuration of the rotation knob provided in the existing handheld instrument for endoscope surgery.

FIG. 14 is a cross-sectional view showing a rotation knob 302 for a shaft provided to a handle 301 included in a general handheld instrument for endoscope surgery, and FIG. 15 is a plan view of the rotation knob 302. As shown in the figures, in the handheld instrument 300, a shaft 303, a jaw driving pipe 304, and an ultrasonic transmission rod 305 are inserted through the rotation knob 302. In the general handheld instrument for endoscope surgery, there is no wiring to be introduced from the shaft 303 into the casing of the handle 301, an introduction hole is not provided to the rotation knob.

Meanwhile, in the handheld instrument 100 according to this embodiment, although there is a need to introduce the signal wiring 140 extending from the ultrasonic transducer array 154 provided to the jaw 150 into the casing of the handle 110, it is possible to introduce the signal wiring 140 by using the introduction hole 112b.

[Regarding Handle]

Figure 16:
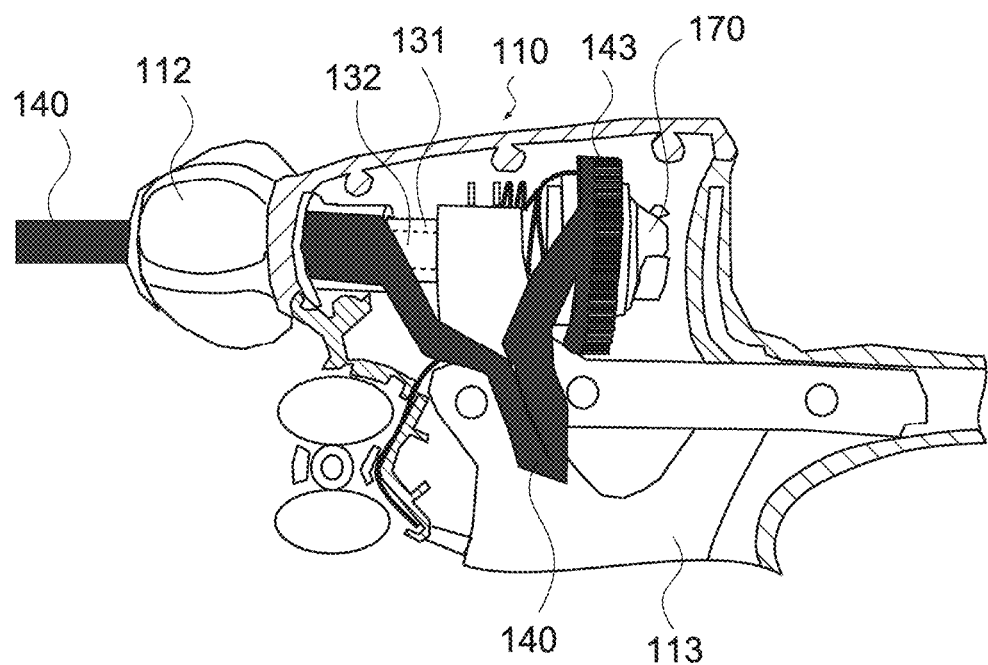
FIG. 16 is a cross-sectional view showing a configuration of a handle provided in the handheld instrument for endoscope surgery according to the embodiment of the present technology.

FIG. 16 is a cross-sectional view of the handle 110. As shown in the figure, an operation mechanism 113 is provided to the handle 110. The jaw driving pipe 131 and the ultrasonic transmission rod 132 are inserted through the casing of the handle 110 via the rotation knob 112, and the jaw driving pipe 131 is connected to the operation mechanism 113. When a user operates the trigger 111 (see FIG. 1) connected to the operation mechanism 113, the operation mechanism 113 operates and rotates the jaw driving pipe 131 back and forth along the extending direction of the shaft 130 to open and close the jaw 150.

At an end portion of the ultrasonic transmission rod 132, an ultrasonic transmission mechanism 170 is provided. The ultrasonic transmission mechanism 170 is acoustically connected to an ultrasonic generator (not shown) mounted on the handle 110, and transmits ultrasonic waves generated by the ultrasonic generator to the ultrasonic transmission rod 132.

As described above, the signal wiring 140 is introduced into the casing of the handle 110 via the introduction hole 112b provided to the rotation knob 112. The signal wiring 140 has a sufficient length so as not to be twisted even in the case where the rotation knob 112 is rotated by 360° or more.

Further, at an end portion of the signal wiring 140, a connector 143 is provided. The connector 143 is a connector for electrically transmitting an output signal of the signal wiring 140, i.e., a signal for the ultrasonic imaging generated by the ultrasonic transducer array 154, to the ultrasonic generator (not shown).

Figure 17:
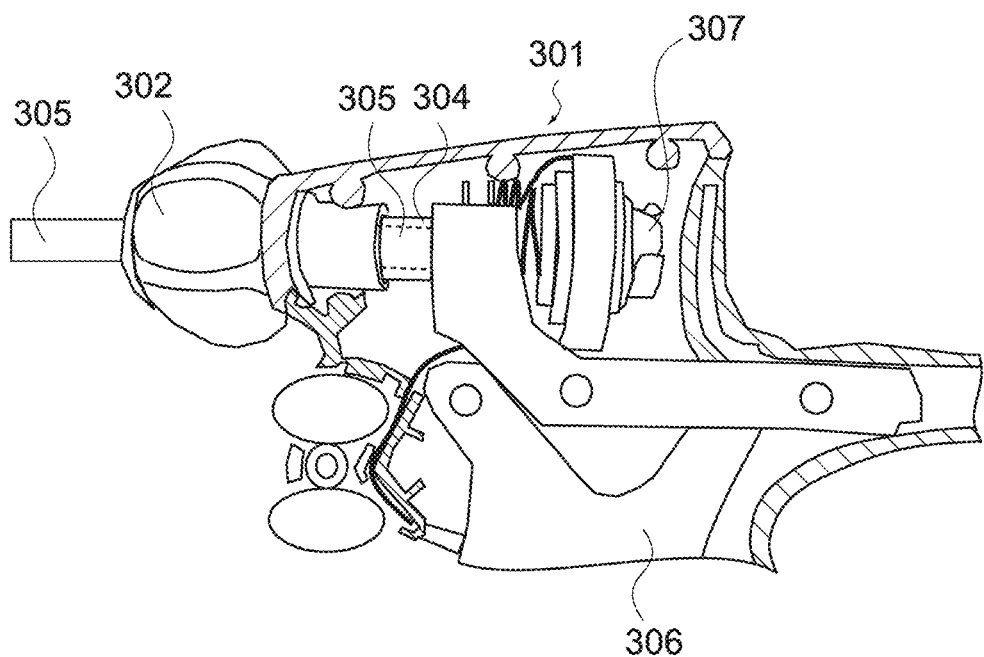
FIG. 17 is a cross-sectional view showing a configuration of a handle provided in an existing handheld instrument for endoscope surgery.

FIG. 17 is a cross-sectional view of the handle 301 of the general handheld instrument for endoscope surgery 300. As shown in the figure, the handle 301 includes the rotation knob 302, the jaw driving pipe 304, the ultrasonic transmission rod 305, and an operation mechanism 306. At an end portion of the ultrasonic transmission rod 305, an ultrasonic transmission mechanism 307 is provided.

The handle 301 is similar to the handle 110 according to this embodiment in that the jaw driving pipe 304 is driven by the operation mechanism 306 and ultrasonic waves are transmitted from the ultrasonic generator (not shown) to the ultrasonic transmission rod 305 by the ultrasonic transmission mechanism 307. However, in the general handheld instrument for endoscope surgery, a signal for imaging or the like is not transmitted from the jaw to the handle, and a signal wiring and a connector are not provided in the handle.

The handheld instrument 100 according to this embodiment has the configuration described above. As described above, the ultrasonic transducer array 154 for the ultrasonic imaging is provided to the jaw 150.

The signal for imaging generated by the ultrasonic transducer array 154 is introduced into the handle 110 via the signal wiring 140, and output from the connector 143 to an external apparatus such as an ultrasonic generator. That is, the handheld instrument 100 has both a function as an instrument for surgery and a function as an ultrasonic sensor for the ultrasonic imaging. Therefore, since it is unnecessary to provide a port for an ultrasonic sensor and the insertion position of the jaw into the body and the insertion position of the ultrasonic sensor match with each other, it is possible to provide high convenience.

[Regarding Configuration of Jaw]

As described above, in the handheld instrument 100 according to an embodiment of the present technology, an ultrasonic sensor for the ultrasonic imaging is mounted on the movable jaw 152. The method of mounting the ultrasonic sensor on the movable jaw is not limited the one described above, and the following method may be employed. Note that in the following embodiments, an ultrasonic sensor including the ultrasonic transducer array 154, the acoustic lens 155, the acoustic matching layer 156, and the backing layer 157 described above will be referred to as ultrasonic sensor 1000.

Another Embodiment 1

Figure 22:
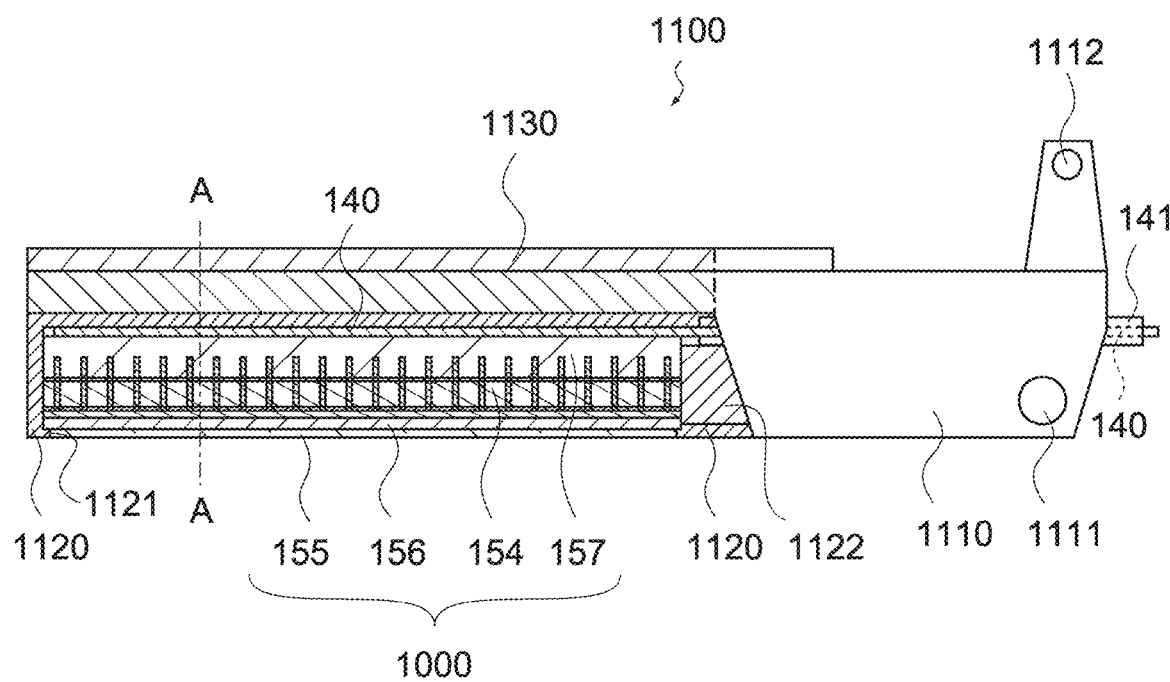
FIG. 22 is a partial cross-sectional view showing a configuration of a jaw according to another embodiment 1 of the present technology.
Figure 23:
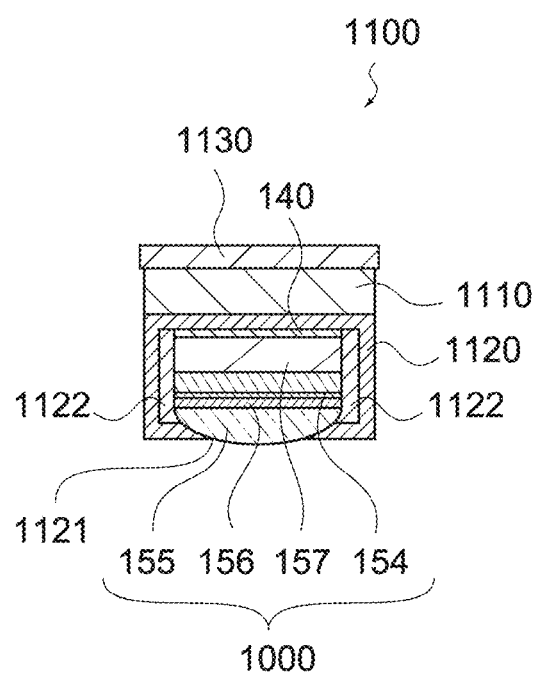
FIG. 23 is a cross-sectional view showing the configuration of the jaw according to another embodiment 1 of the present technology.

FIG. 22 and FIG. 23 are each a schematic diagram of a movable jaw 1100 according to another embodiment 1 of the present technology. FIG. 22 is a partial cross-sectional view of the movable jaw 1100 as seen from the direction perpendicular to the extending direction of the shaft 130, and FIG. 23 is a cross-sectional view of the movable jaw 1100 taken along the line A-A in FIG. 22 as seen from the extending direction of the shaft 130.

As shown in the figures, the movable jaw 1100 includes a jaw main body 1110, a casing 1120, a tissue pad 1130, and the ultrasonic sensor 1000.

The jaw main body 1110 is a member that is connected to the shaft 130 and serves as a base portion of the movable jaw 1100. The jaw main body 1110 may be formed of metal such as stainless steel. The jaw main body 1110 includes a hole 1111 for inserting a pin thereinto and a claw 1112 supported by the shaft 130. These are used for opening and closing the movable jaw 1100 by the operation of the jaw driving pipe 131.

The claw 1112 may be a separate part from the jaw main body 1110, and fixed to the jaw main body 1110 by spot welding with silver wax, laser, or the like. Further, the jaw main body 1110 may be formed by cutting out stainless steel, and the hole 1111 may be formed by bending a metal plate.

The casing 1120 is mounted on the jaw main body 1110, and houses the ultrasonic sensor 1000. The casing 1120 may be formed of biocompatible resin such as ABS (Acrylonitrile/Butadiene/Styrene copolymer), nylon resin, PTFE (polytetrafluoroethylene), and noryl, a metal material such as stainless steel and a Ti-based material, or the like.

As shown in FIG. 22 and FIG. 23, the casing 1120 has a shape covering the entire periphery of the ultrasonic sensor 1000 except that it has an opening 1121 that exposes the acoustic lens 155. Between the casing 1120 and the ultrasonic sensor 1000, a filler 1122 formed of silicone or the like is filled. Note that in the casing 1120, a supporting member (see another embodiment 6) having a higher rigidity than the ultrasonic sensor 1000 may be housed together with the ultrasonic sensor 1000.

The casing 1120 is adhered to the jaw main body 1110 by a medical adhesive. As the medical adhesive, epoxy resin, polyurethane resin, cyanoacrylate resin, silicone resin, or the like can be used. The medical adhesive is used for adhering injection needles or catheter balloons, and has little effect on human bodies.

The tissue pad 1130 is mounted on the side of the jaw main body 1110 opposite to the casing 1120. The tissue pad 1130 is formed of a material having a low thermal conductivity such as polyurethane. The tissue pad 1130 is adhered to the jaw main body 1110 by the medical adhesive as described above.

The movable jaw 1100 has the configuration described above. As described above, the ultrasonic sensor 1000 is formed of an electronic material such as PZT, and such an electronic material is not permitted to be exposed in a living body. However, by covering it with the casing 1120, it is possible to prevent the electronic material to be exposed, and maintain the biocompatibility of the movable jaw 1100.

Further, as described above, the probe 151 generates heat by generating ultrasonic vibration, and the temperature thereof rises to approximately 200° C. However, by forming the tissue pad 1130 of polyurethane or the like having a low thermal conductivity, it is possible to reduce the temperature of the movable jaw 1100 to approximately 42° C. This temperature is lower than the heat-resistant temperature of most medical adhesives, so that no problem occurs.

Another Embodiment 2

Figure 24:
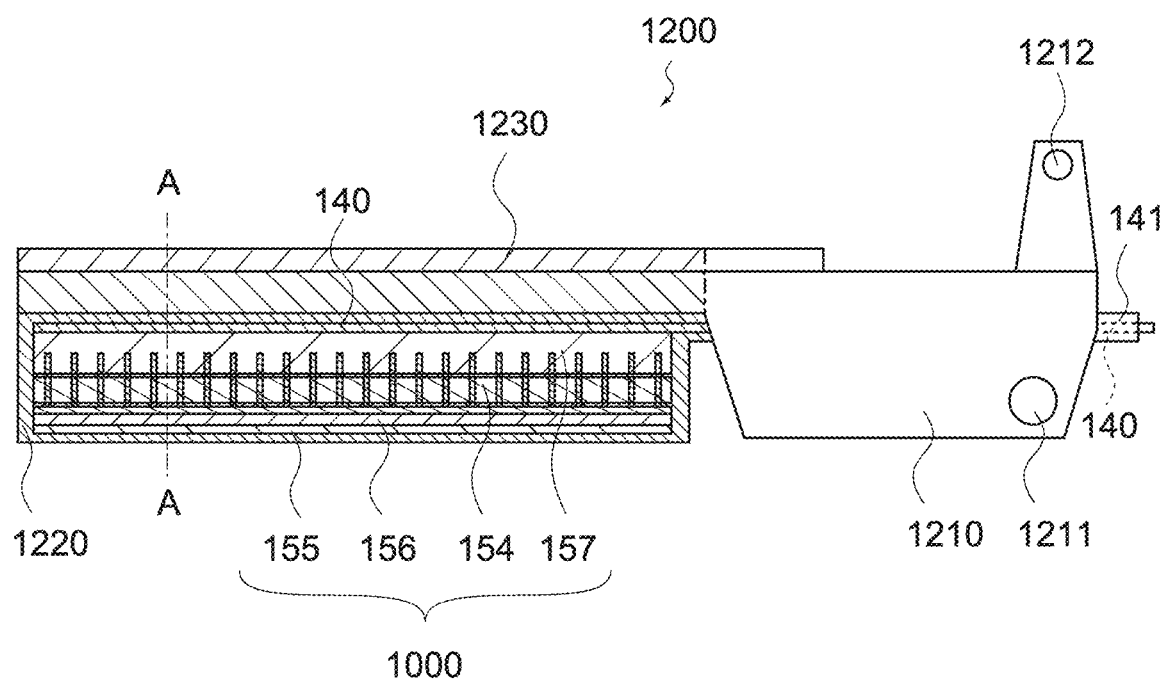
FIG. 24 is a partial cross-sectional view showing a configuration of a jaw according to another embodiment 2 of the present technology.
Figure 25:
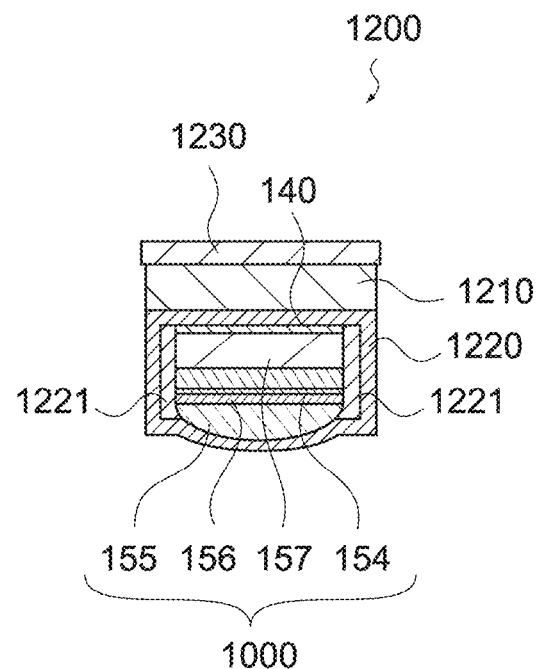
FIG. 25 is a cross-sectional view showing the configuration of the jaw according to another embodiment 2 of the present technology.

FIG. 24 and FIG. 25 are each a schematic diagram of a movable jaw 1200 according to another embodiment 2 of the present technology. FIG. 24 is a partial cross-sectional view of the movable jaw 1200 as seen from the direction perpendicular to the extending direction of the shaft 130, and FIG. 25 is a cross-sectional view of the movable jaw 1200 taken along the line A-A in FIG. 24 as seen from the extending direction of the shaft 130.

As shown in the figures, the movable jaw 1200 includes a jaw main body 1210, a thermal contraction tube 1220, a tissue pad 1230, and the ultrasonic sensor 1000.

The jaw main body 1210 is a member that is connected to the shaft 130 and serves as a base portion of the movable jaw 1100. The jaw main body 1210 may be formed of metal such as stainless steel. The jaw main body 1210 includes a hole 1211 for inserting a pin thereinto and a claw 1212 supported by the shaft 130. These are used for opening and closing the movable jaw 1200 by the operation of the jaw driving pipe 131.

The claw 1212 may be a separate part from the jaw main body 1210, and fixed to the jaw main body 1210 by spot welding with silver wax, laser, or the like. Further, the jaw main body 1210 may be formed by cutting out stainless steel, and the hole 1211 may be formed by bending a metal plate.

The thermal contraction tube 1220 is mounted on the jaw main body 1210 and houses the ultrasonic sensor 1000. The thermal contraction tube 1220 may be formed of a biocompatible material having thermal contraction characteristics, such as PVDF (PolyVinylidene DiFluoride), nylon resin, and PTFE.

As shown in FIG. 24 and FIG. 25, the thermal contraction tube 1220 tube has a shape covering the entire periphery of the ultrasonic sensor 1000. Further, the thermal contraction tube 1220 functions as also the covering member 141 by covering the ultrasonic sensor 1000 and the signal wiring 140, which makes it possible to omit a production step and reduce the production cost. Between the thermal contraction tube 1220 and the ultrasonic sensor 1000, a filler 1221 formed of silicone or the like is filled. Note that in the thermal contraction tube 1220, a supporting member (see another embodiment 6) having a higher rigidity than the ultrasonic sensor 1000 may be housed together with the ultrasonic sensor 1000.

The thermal contraction tube 1220 is adhered to the jaw main body 1210 by a medical adhesive. As the medical adhesive, epoxy resin, polyurethane resin, cyanoacrylate resin, silicone resin, or the like can be used. The medical adhesive is used for adhering injection needles or catheter balloons, and has little effect on human bodies.

The tissue pad 1230 is mounted on the side of the jaw main body 1210 opposite to the thermal contraction tube 1220. The tissue pad 1230 is formed of a material having a low thermal conductivity such as polyurethane. The tissue pad 1230 is adhered to the jaw main body 1210 by the medical adhesive as described above.

The movable jaw 1200 has the configuration described above. As described above, the ultrasonic sensor 1000 is formed of an electronic material such as PZT, and such an electronic material is not permitted to be exposed in a living body. However, by covering it with the thermal contraction tube 1220, it is possible to prevent the electronic material to be exposed, and maintain the biocompatibility of the movable jaw 1200.

Further, as described above, the probe 151 generates heat by generating ultrasonic vibration, and the temperature thereof rises to approximately 200° C. However, by forming the tissue pad 1330 of polyurethane or the like having a low thermal conductivity, it is possible to reduce the temperature of the movable jaw 1300 to approximately 42° C. This temperature is lower than the heat-resistant temperature of most medical adhesives, so that no problem occurs.

Note that the thermal contraction tube 1220 may be formed of the same material as that of the acoustic lens 155. In this case, it is also possible to form a material such as a nylon-based material and thermal contraction silicone into a shape having acoustic focusing property in advance when forming it into a tube shape.

Another Embodiment 3

Figure 26:
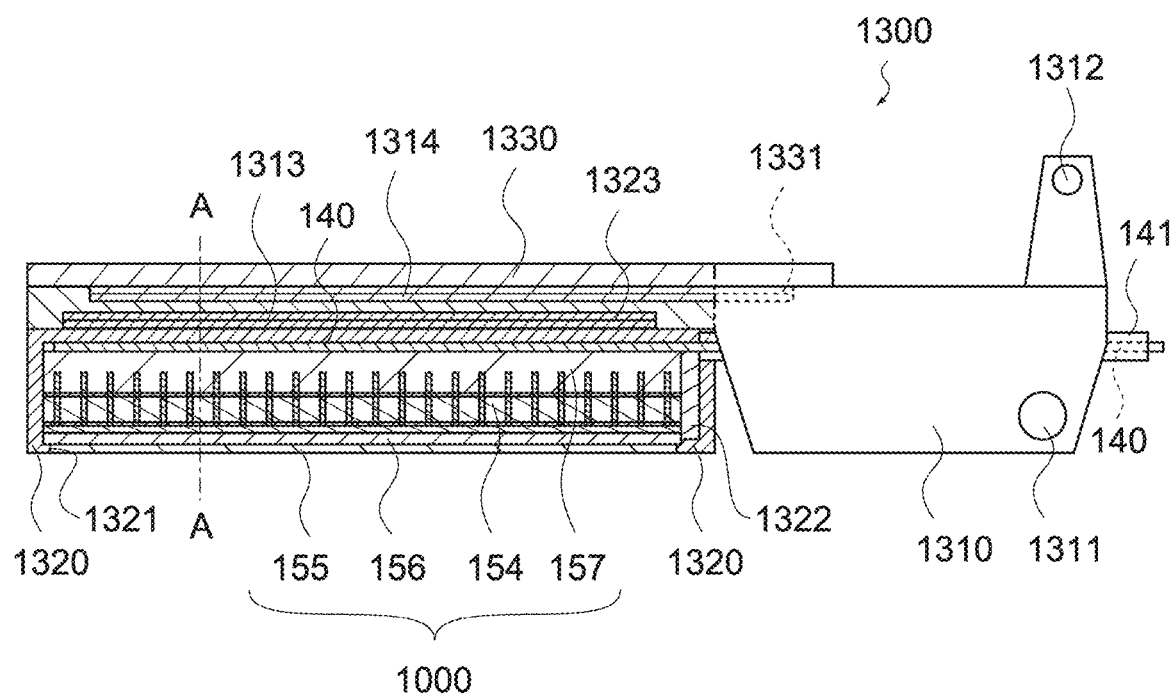
FIG. 26 is a partial cross-sectional view showing a configuration of a jaw according to another embodiment 3 of the present technology.
Figure 27:
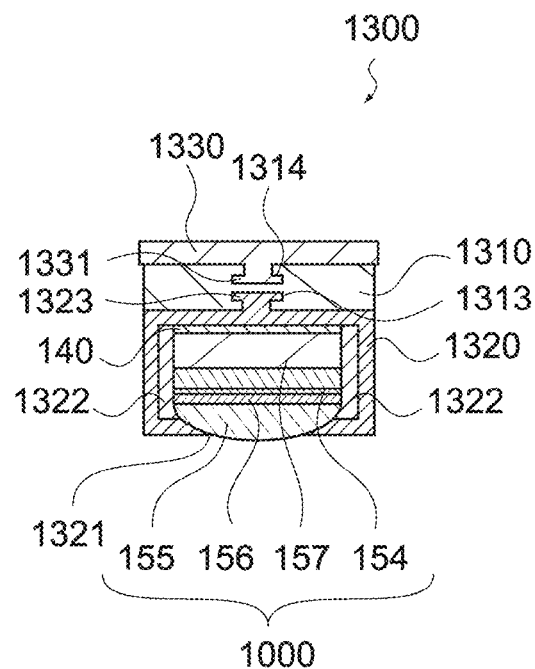
FIG. 27 is a cross-sectional view showing the configuration of the jaw according to another embodiment 3 of the present technology.

FIG. 26 and FIG. 26 are each a schematic diagram of a movable jaw 1300 according to another embodiment 3 of the present technology. FIG. 26 is a partial cross-sectional view of the movable jaw 1300 as seen from the direction perpendicular to the extending direction of the shaft 130, and FIG. 27 is a cross-sectional view of the movable jaw 1300 taken along the line A-A in FIG. 26 as seen from the extending direction of the shaft 130.

As shown in the figure, the movable jaw 1300 includes a jaw main body 1310, a casing 1320, a tissue pad 1330, and the ultrasonic sensor 1000.

The jaw main body 1310 is a member that is connected to the shaft 130 and serves as a base portion of the movable jaw 1300. The jaw main body 1310 may be formed of metal such as stainless steel. The jaw main body 1310 includes a hole 1311 for inserting a pin thereinto and a claw 1312 supported by the shaft 130. These are used for opening and closing the movable jaw 1300 by the operation of the jaw driving pipe 131.

The claw 1312 may be a separate part from the jaw main body 1310, and fixed to the jaw main body 1310 by spot welding with silver wax, laser, or the like. Further, the jaw main body 1310 may be formed by cutting out stainless steel, and the hole 1311 may be formed by bending a metal plate.

Further, in the jaw main body 1310, a recessed portion 1313 and a recessed portion 1314 that extend along the extending direction of the shaft 130 are provided. As shown in FIG. 27, the recessed portion 1313 and the recessed portion 1314 may each have a groove shape having a T-shaped cross section. Further, a plurality of recessed portions 1313 and a plurality of recessed portions 1314 may be provided.

The casing 1320 is mounted on the jaw main body 1310 and houses the ultrasonic sensor 1000. The casing 1320 may be formed of biocompatible resin such as ABS, nylon resin, PTFE, and noryl, a metal material such as stainless steel and a Ti-based material, or the like.

As shown in FIG. 26 and FIG. 27, the casing 1320 has a shape covering the entire periphery of the ultrasonic sensor 1000 except that it has an opening 1321 that exposes the acoustic lens 155. Between the casing 1320 and the ultrasonic sensor 1000, a filler 1322 formed of silicone or the like is filled. Note that in the casing 1320, a supporting member (see another embodiment 6) having a higher rigidity than the ultrasonic sensor 1000 may be housed together with the ultrasonic sensor 1000.

Further, the casing 1320 includes a projecting portion 1323 that extends along the extending direction of the shaft 130. The projecting portion 1323 has a shape engaging with the recessed portion 1313 provided to the jaw main body 1310. The projecting portion 1323 engages with the recessed portion 1313, and thus, the casing 1320 is mounted on the jaw main body 1310.

The tissue pad 1330 is mounted on the side of the jaw main body 1310 opposite to the casing 1320. The tissue pad 1330 is formed of a material having a low thermal conductivity such as polyurethane.

Further, the tissue pad 1330 includes a projecting portion 1331 that extends along the extending direction of the shaft 130. The projecting portion 1331 has a shape engaging with the recessed portion 1314 provided to the jaw main body 1310. The projecting portion 1331 engages with the recessed portion 1314, and thus, the tissue pad 1330 is mounted on the jaw main body 1310.

The movable jaw 1100 has the configuration described above. As described above, the ultrasonic sensor 1000 is formed of an electronic material such as PZT, and such an electronic material is not permitted to be exposed in a living body. However, by covering it with the casing 1320, it is possible to prevent the electronic material to be exposed, and maintain the biocompatibility of the movable jaw 1300.

Further, as described above, the probe 151 generates heat by generating ultrasonic vibration, and the temperature thereof rises to approximately 200° C. However, the casing 1320 and the tissue pad 1330 are mounted on the jaw main body 1310 by the engagement of the recessed portion and the projecting portion, and no adhesive is used for the mounting of these, which suppresses the influence by heat generation.

Note that instead of the above-mentioned configuration, recessed portions may be provided to the casing 1320 and the tissue pad 1330, and projecting portions that engage with these recessed portions may be provided to the jaw main body 1310.

Another Embodiment 4

Figure 28:
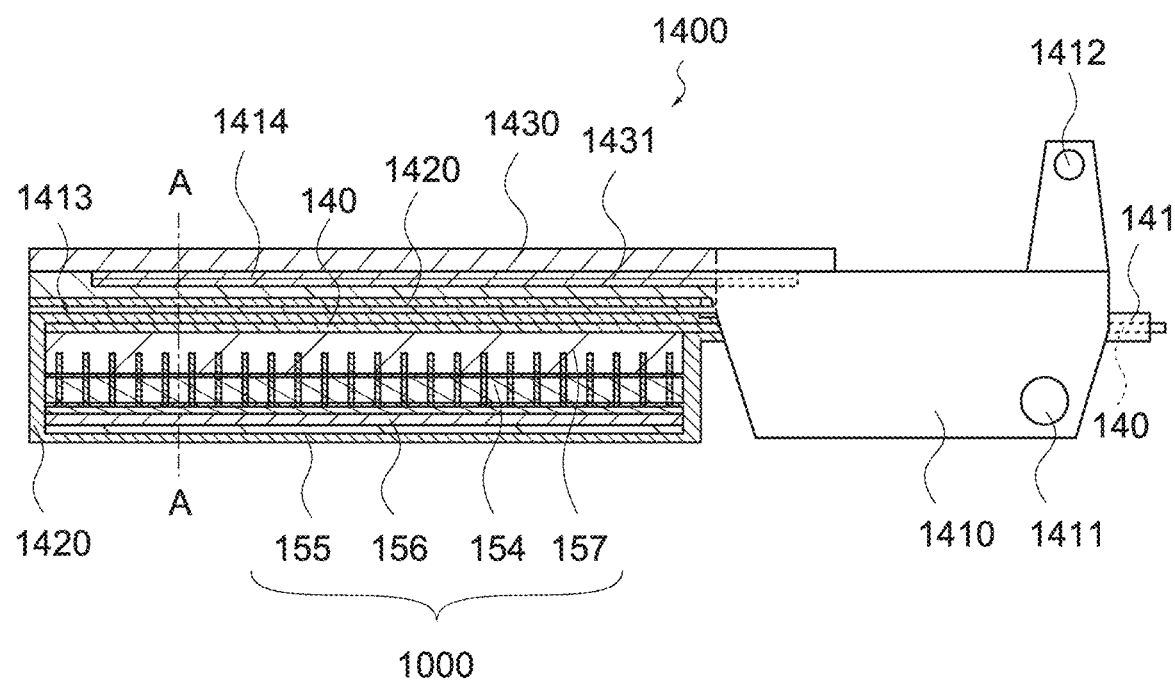
FIG. 28 is a partial cross-sectional view showing a configuration of a jaw according to another embodiment 4 of the present technology.
Figure 29:
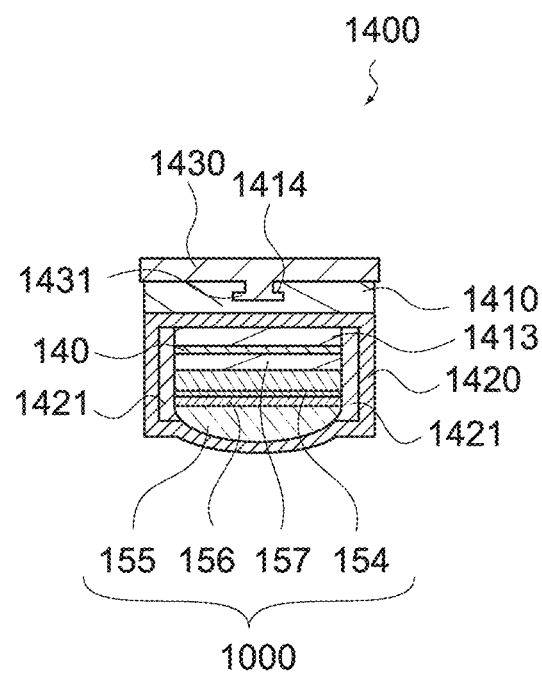
FIG. 29 is a cross-sectional view showing the configuration of the jaw according to another embodiment 4 of the present technology.

FIG. 28 and FIG. 29 are each a schematic diagram of a movable jaw 1400 according to another embodiment 4 of the present technology. FIG. 28 is a partial cross-sectional view of the movable jaw 1400 as seen from the direction perpendicular to the extending direction of the shaft 130, and FIG. 29 is a cross-sectional view of the movable jaw 1400 taken along the line A-A in FIG. 28 as seen from the extending direction of the shaft 130.

As shown in the figures, the movable jaw 1400 includes a jaw main body 1410, a thermal contraction tube 1420, a tissue pad 1430, and the ultrasonic sensor 1000.

The jaw main body 1410 is a member that is connected to the shaft 130 and serves as a base portion of the movable jaw 1100. The jaw main body 1410 may be formed of metal such as stainless steel. The jaw main body 1410 includes a hole 1411 for inserting a pin thereinto and a claw 1412 supported by the shaft 130. These are used for opening and closing the movable jaw 1400 by the operation of the jaw driving pipe 131.

The claw 1412 may be a separate part from the jaw main body 1410, and fixed to the jaw main body 1410 by spot welding with silver wax, laser, or the like. Further, the jaw main body 1410 may be formed by cutting out stainless steel, and the hole 1411 may be formed by bending a metal plate.

Figure 30:
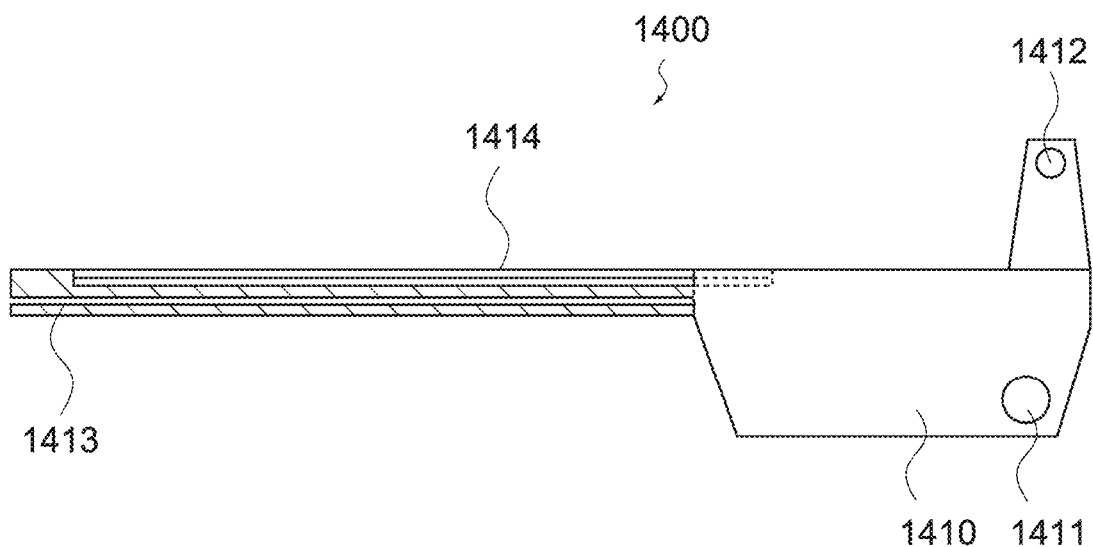
FIG. 30 is a cross-sectional view showing a configuration of a jaw main body provided in the jaw according to another embodiment 4 of the present technology.

FIG. 30 is a cross-sectional view showing the jaw main body 1410. As shown in the figure, a split end portion 1413 is provided to the jaw main body 1410. The split end portion 1413 is provided at a tip portion of the jaw main body 1410, and apart from the main body portion of the jaw main body 1410 except the base portion. Two or more split end portions 1413 may be provided.

Further, to the jaw main body 1410, a recessed portion 1414 that extends along the extending direction of the shaft 130 is provided. As shown in FIG. 29, the recessed portion 1414 may have a groove shape having a T-shaped cross section. Further, a plurality of recessed portions 1414 may be provided.

The thermal contraction tube 1420 is mounted on the jaw main body 1410, and houses the ultrasonic sensor 1000. The thermal contraction tube 1420 may be formed of a biocompatible material having thermal contraction characteristics, such as PVDF, nylon resin, and PTFE.

As shown in FIG. 28 and FIG. 29, the thermal contraction tube 1420 covers the ultrasonic sensor 1000 and the split end portion 1413. Further, the thermal contraction tube 1420 functions as also the covering member 141 by covering them and also the signal wiring 140, which makes it possible to omit a production step and reduce the production cost. Between the thermal contraction tube 1420 and the ultrasonic sensor 1000, a filler 1421 formed of silicone or the like is filled. Note that in the thermal contraction tube 1420, a supporting member (see another embodiment 6) having a higher rigidity than the ultrasonic sensor 1000 may be housed together with the ultrasonic sensor 1000.

The thermal contraction tube 1420 is mounted on the jaw main body 1410 by covering the ultrasonic sensor 1000 and the split end portion 1413.

The tissue pad 1430 is mounted on the side of the jaw main body 1410 opposite to the thermal contraction tube 1420. The tissue pad 1430 is formed of a material having a low thermal conductivity such as polyurethane. Further, the tissue pad 1430 includes a projecting portion 1431 that extends along the extending direction of the shaft 130. The projecting portion 1431 has a shape engaging with the recessed portion 1414 provided to the jaw main body 1410. The projecting portion 1431 engages with the recessed portion 1414, and thus, the tissue pad 1430 is mounted on the jaw main body 1410.

The movable jaw 1400 has the configuration described above. As described above, the ultrasonic sensor 1000 is formed of an electronic material such as PZT, and such an electronic material is not permitted to be exposed in a living body. However, by covering it with the thermal contraction tube 1420, it is possible to prevent the electronic material to be exposed, and maintain the biocompatibility of the movable jaw 1400.

Further, as described above, the probe 151 generates heat by generating ultrasonic vibration, and the temperature thereof rises to approximately 200° C. However, the thermal contraction tube 1420 and the tissue pad 1430 are mounted on the jaw main body 1410 by a method other than adhesion, and no adhesive is used, which suppresses the influence by heat generation.

Note that instead of the above-mentioned configuration, a recessed portion may be provided to the tissue pad 1430, and a projecting portion that engage with the recessed portion may be provided to the jaw main body 1410.

Another Embodiment 5

Figure 31:
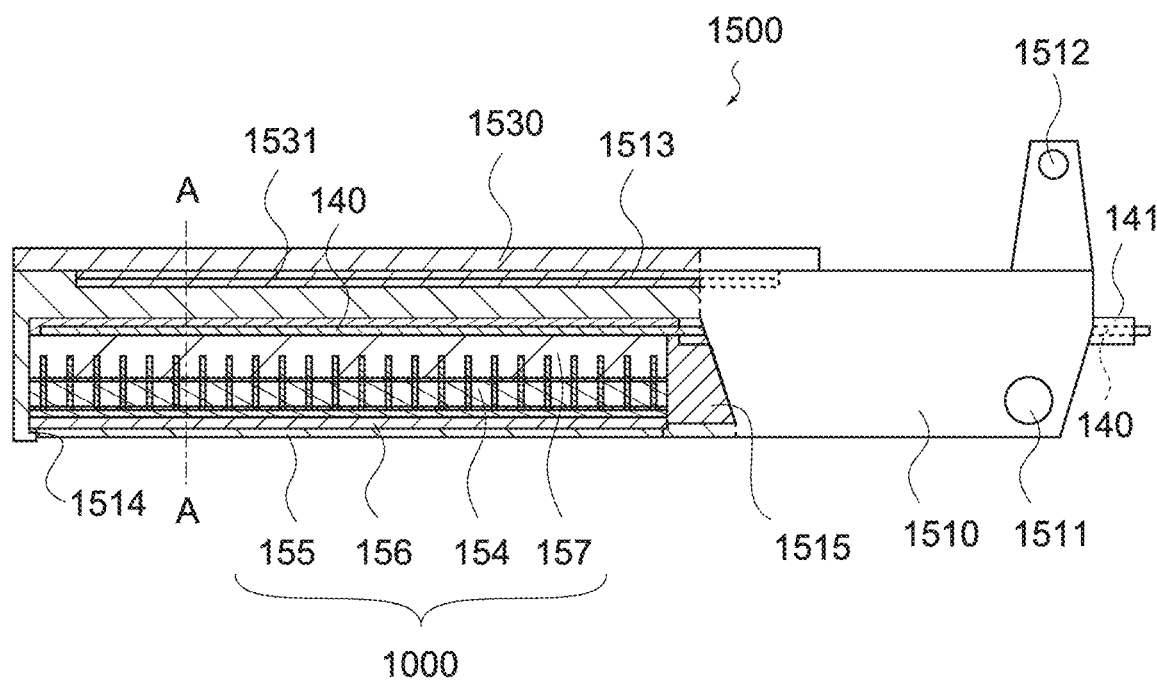
FIG. 31 is a partial cross-sectional view showing a configuration of a jaw according to another embodiment 5 of the present technology.
Figure 32:
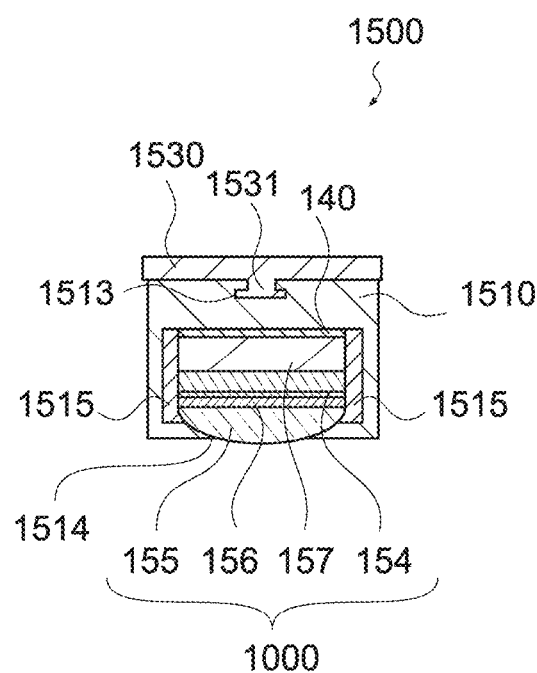
FIG. 32 is a cross-sectional view showing the configuration of the jaw according to another embodiment 5 of the present technology.

FIG. 31 and FIG. 32 are each a schematic diagram showing a movable jaw 1500 according to another embodiment 5 of the present technology. FIG. 31 is a partial cross-sectional view of the movable jaw 1500 as seen from the direction perpendicular to the extending direction of the shaft 130, and FIG. 32 is a cross-sectional view of the movable jaw 1500 taken along the line A-A in FIG. 31 as seen from the extending direction of the shaft 130.

As shown in the figures, the movable jaw 1500 includes a jaw main body 1510, a tissue pad 1530, and the ultrasonic sensor 1000.

The jaw main body 1510 is a member that is connected to the shaft 130 and serves as a base portion of the movable jaw 1500. The jaw main body 1510 may be formed of metal such as stainless steel. The jaw main body 1510 includes a hole 1511 for inserting a pin thereinto and a claw 1512 supported by the shaft 130. These are used for opening and closing the movable jaw 1500 by the operation of the jaw driving pipe 131.

The claw 1512 may be a separate part from the jaw main body 1510, and fixed to the jaw main body 1510 by spot welding with silver wax, laser, or the like. Further, the jaw main body 1510 may be formed by cutting out stainless steel, and the hole 1511 may be formed by bending a metal plate.

Further, to the jaw main body 1510, a recessed portion 1513 that extends along the extending direction of the shaft 130 is provided. As shown in FIG. 32, the recessed portion 1513 may have a groove shape having a T-shaped cross section. Further, a plurality of recessed portions 1513 may be provided.

The jaw main body 1510 houses the ultrasonic sensor 1000. As shown in FIG. 31 and FIG. 32, the jaw main body 1510 has a shape covering the entire periphery of the ultrasonic sensor 1000 except that it has an opening 1514 that exposes the acoustic lens 155. Between the jaw main body 1510 and the ultrasonic sensor 1000, a filler 1515 formed of silicone or the like is filled. Note that in the jaw main body 1510, a supporting member (see another embodiment 6) having a higher rigidity than the ultrasonic sensor 1000 may be housed together with the ultrasonic sensor 1000.

By making the jaw main body 1510 function as a casing that houses the ultrasonic sensor 1000, it is unnecessary to adhere a casing with an adhesive and it is easy to secure the depth of the recessed portion 1513.

The tissue pad 1530 is mounted on the side of the jaw main body 1510 opposite to the ultrasonic sensor 1000. The tissue pad 1130 is formed of a material having a low thermal conductivity such as polyurethane. Further, the tissue pad 1530 includes a projecting portion 1531 that extends along the extending direction of the shaft 130. The projecting portion 1531 has a shape engaging with the recessed portion 1513 provided to the jaw main body 1510. The projecting portion 1531 engages with the recessed portion 1513, and thus, the tissue pad 1530 is mounted on the jaw main body 1510.

The movable jaw 1500 has the configuration described above. As described above, the ultrasonic sensor 1000 is formed of an electronic material such as PZT, and such an electronic material is not permitted to be exposed in a living body. However, by covering it with the jaw main body 1510, it is possible to prevent the electronic material to be exposed, and maintain the biocompatibility of the movable jaw 1500.

Further, as described above, the probe 151 generates heat by generating ultrasonic vibration, and the temperature thereof rises to approximately 200° C. However, the tissue pad 1530 is mounted on the jaw main body 1510 by a method other than adhesion, and no adhesive is used, which suppresses the influence by heat generation.

Further, by using the jaw main body 1510 as a casing of the ultrasonic sensor 1000, it is possible to omit the attachment portion between the jaw main body 1510 and the casing, reduce the thickness of the movable jaw 1500, and enhance the rigidity.

Note that instead of the above-mentioned configuration, a recessed portion may be provided to the tissue pad 1530, and a projecting portion that engage with the recessed portion may be provided to the jaw main body 1510.

Another Embodiment 6

Figure 33:
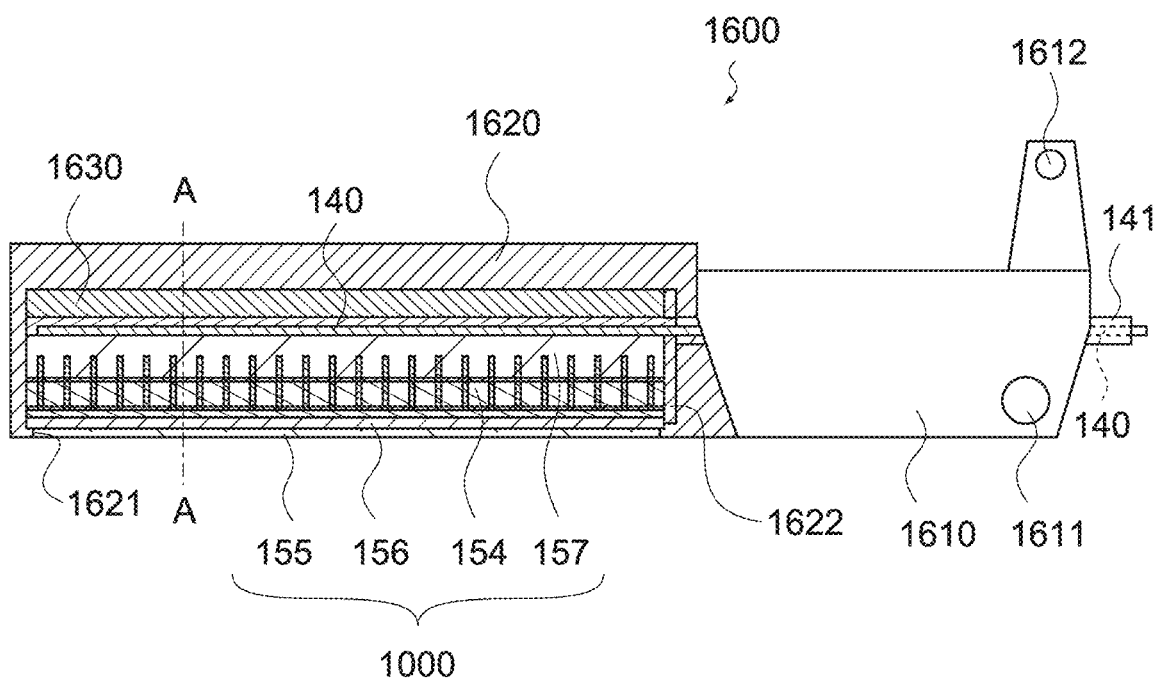
FIG. 33 is a partial cross-sectional view showing a configuration of a jaw according to another embodiment 6 of the present technology.
Figure 34:
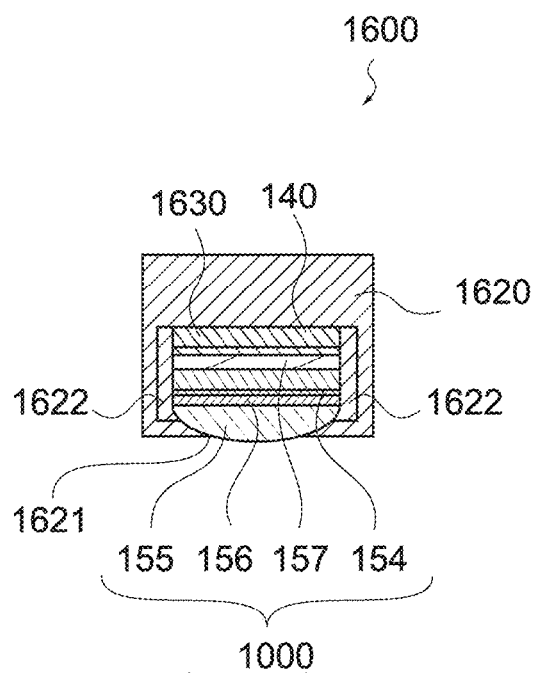
FIG. 34 is a cross-sectional view showing the configuration of the jaw according to another embodiment 6 of the present technology.

FIG. 33 and FIG. 34 are each a schematic diagram showing a movable jaw 1600 according to another embodiment 6 of the present technology. FIG. 33 is a partial cross-sectional view of the movable jaw 1600 as seen from the direction perpendicular to the extending direction of the shaft 130, and FIG. 34 is a cross-sectional view of the movable jaw 1600 taken along the line A-A in FIG. 33 as seen from the extending direction of the shaft 130.

As shown in the figures, the movable jaw 1600 includes a jaw main body 1610, a tissue pad and casing 1620, a supporting member 1630 and the ultrasonic sensor 1000.

The jaw main body 1610 is a member that is connected to the shaft 130 and serves as a base portion of the movable jaw 1600. The jaw main body 1610 may be formed of metal such as stainless steel. The jaw main body 1610 includes a hole 1611 for inserting a pin thereinto and a claw 1612 supported by the shaft 130. These are used for opening and closing the movable jaw 1600 by the operation of the jaw driving pipe 131.

The claw 1612 may be a separate part from the jaw main body 1610, and fixed to the jaw main body 1610 by spot welding with silver wax, laser, or the like. Further, the jaw main body 1610 may be formed by cutting out stainless steel, and the hole 1611 may be formed by bending a metal plate.

The tissue pad and casing 1620 is fixed to the jaw main body 1610, and houses the ultrasonic sensor 1000. As shown in FIG. 33 and FIG. 34, the tissue pad and casing 1620 has a shape covering the entire periphery of the ultrasonic sensor 1000 except that it has an opening 1621 that exposes the acoustic lens 155. Between the tissue pad and casing 1620 and the ultrasonic sensor 1000, a filler 1622 formed of silicone or the like is filled.

The tissue pad and casing 1620 is formed of polyurethane. Accordingly, the surface of the tissue pad and casing 1620 opposite to the ultrasonic sensor 1000 can be used as a tissue pad. The tissue pad and casing 1620 formed of polyurethane and the jaw main body 1610 formed of metal can be integrally formed by a multi-stage molding step such as insert molding.

The supporting member 1630 is a member having a rigidity higher than that of the ultrasonic sensor 1000, and housed in the tissue pad and casing 1620 together with the ultrasonic sensor 1000. The supporting member 1630 may be a stainless steel plate having a thickness of 0.3 mm, for example. Alternatively, the supporting member 1630 may be formed a material having a high rigidity such as a Ti alloy and ceramic.

As described above, since the tissue pad and casing 1620 is formed of polyurethane, when the jaw is held, the jaw is bend, and the inside of the movable jaw or the ultrasonic sensor may be damaged. However, by placing the supporting member 1630, the strength of the movable jaw 1600 is secured, and such a problem can be avoided.

The movable jaw 1600 has the configuration described above. As described above, the ultrasonic sensor 1000 is formed of an electronic material such as PZT, and such an electronic material is not permitted to be exposed in a living body. However, by covering it with the tissue pad and casing 1620, it is possible to prevent the electronic material to be exposed, and maintain the biocompatibility of the movable jaw 1600.

Further, as described above, the probe 151 generates heat by generating ultrasonic vibration, and the temperature thereof rises to approximately 200° C. However, no adhesive is used for fixing the tissue pad and casing 1620 and the jaw main body 1610, which suppresses the influence by heat generation.

Another Embodiment 7

Figure 35:
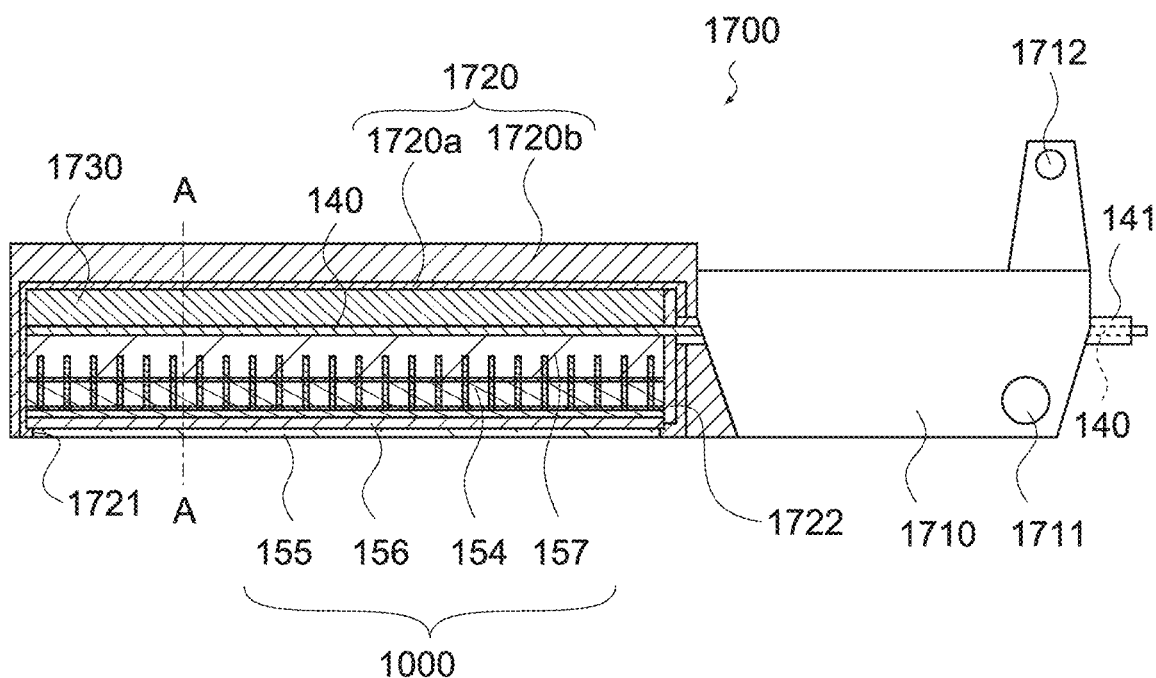
FIG. 35 is a partial cross-sectional view showing a configuration of a jaw according to another embodiment 7 of the present technology.
Figure 36:
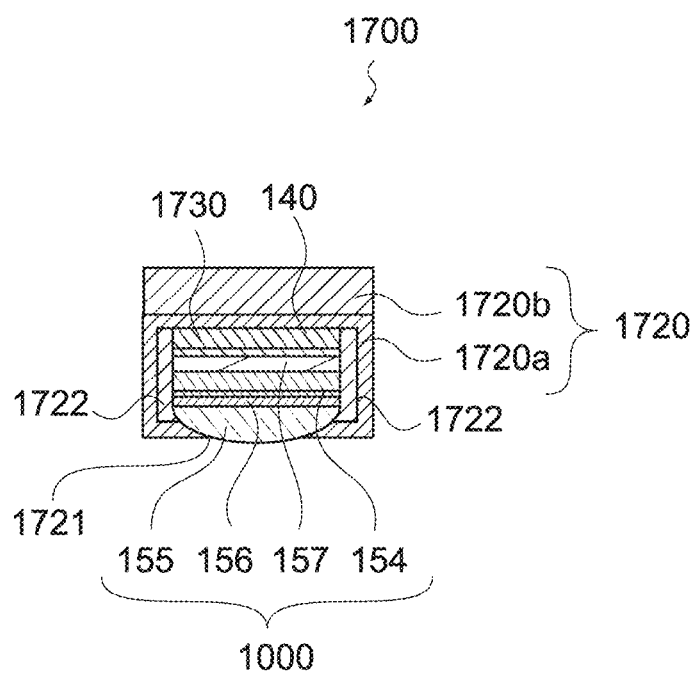
FIG. 36 is a cross-sectional view showing the configuration of the jaw according to another embodiment 7 of the present technology.

FIG. 35 and FIG. 36 are each a schematic diagram showing a movable jaw 1700 according to another embodiment 7 of the present technology. FIG. 35 is a partial cross-sectional view of the movable jaw 1700 as seen from the direction perpendicular to the extending direction of the shaft 130, and FIG. 36 is a cross-sectional view of the movable jaw 1700 taken along the line A-A in FIG. 35 as seen from the extending direction of the shaft 130.

As shown in the figures, the movable jaw 1700 includes a jaw main body 1710, a tissue pad and casing 1720, a supporting member 1730 and the ultrasonic sensor 1000.

The jaw main body 1710 is a member that is connected to the shaft 130 and serves as a base portion of the movable jaw 1700. The jaw main body 1710 may be formed of metal such as stainless steel. The jaw main body 1710 includes a hole 1711 for inserting a pin thereinto and a claw 1712 supported by the shaft 130. These are used for opening and closing the movable jaw 1700 by the operation of the jaw driving pipe 131.

The claw 1712 may be a separate part from the jaw main body 1710, and fixed to the jaw main body 1710 by spot welding with silver wax, laser, or the like. Further, the jaw main body 1710 may be formed by cutting out stainless steel, and the hole 1711 may be formed by bending a metal plate.

The tissue pad and casing 1720 is fixed to the jaw main body 1710, and houses the ultrasonic sensor 1000.

The tissue pad and casing 1720 includes a casing portion 1720*a* and a tissue pad portion 1720*b*. The casing portion 1720*a* is formed of biocompatible resin such as ABS, nylon resin, PTFE, and noryl, and the tissue pad portion 1720*b* is formed of polyurethane. The casing portion 1720*a* and the tissue pad portion 1720*b* are integrally formed by two-color molding to constitute the tissue pad and casing 1720.

As shown in FIG. 35 and FIG. 36, the casing portion 1720*a* has a shape covering the entire periphery of the ultrasonic sensor 1000 except that it has an opening 1721 that exposes the acoustic lens 155. Between the casing portion 1720*a* and the ultrasonic sensor 1000, a filler 1722 formed of silicone or the like is filled. The tissue pad portion 1720*b* is formed of polyurethane, and functions as a tissue pad.

The tissue pad and casing 1720 formed of resin and the jaw main body 1710 formed of metal can be integrally formed by a multi-stage molding step such as insert molding.

The supporting member 1730 is a member having a rigidity higher than that of the ultrasonic sensor 1000, and housed in the tissue pad and casing 1720 together with the ultrasonic sensor 1000. The supporting member 1730 may be a stainless steel plate having a thickness of 0.3 mm, for example. Alternatively, the supporting member 1730 may be formed a material having a high rigidity such as a Ti alloy and ceramic.

As described above, since the tissue pad and casing 1720 is formed of synthetic resin, when the jaw is held, the jaw is bend, and the inside of the movable jaw or the ultrasonic sensor may be damaged. However, by placing the supporting member 1730, the strength of the movable jaw 1700 is secured, and such a problem can be avoided.

The movable jaw 1700 has the configuration described above. As described above, the ultrasonic sensor 1000 is formed of an electronic material such as PZT, and such an electronic material is not permitted to be exposed in a living body. However, by covering it with the tissue pad and casing 1720, it is possible to prevent the electronic material to be exposed, and maintain the biocompatibility of the movable jaw 1700.

Further, as described above, the probe 151 generates heat by generating ultrasonic vibration, and the temperature thereof rises to approximately 200° C. However, no adhesive is used for fixing the tissue pad and casing 1720 and the jaw main body 1710, which suppresses the influence by heat generation.

It should be noted that the present technology may take the following configurations.

(1)

A handheld instrument for endoscope surgery, including:
a shaft;
a jaw that is placed at one end of the shaft and has a holding function;
a handle that is placed at the other end of the shaft and includes an operation mechanism for operating the jaw;
a phased array ultrasonic sensor that is mounted on the jaw and has an imaging function; and
a signal wiring that is provided to the shaft and connects the ultrasonic sensor and the handle.

(2)

The handheld instrument for endoscope surgery according to (1) above, in which
the signal wiring is a flexible printed circuit board, the handheld instrument for endoscope surgery further including
a sealing member for sealing a portion of the signal wiring led out from the jaw.

(3)

The handheld instrument for endoscope surgery according to (1) or (2) above, further including
a covering member for covering a part of the signal wiring, the part of the signal wiring extending between the jaw and the shaft.

(4)

The handheld instrument for endoscope surgery according to any one of (1) to (3) above, in which
the signal wiring is placed on an outer peripheral surface of the shaft.

(5)

The handheld instrument for endoscope surgery according to any one of (1) to (4) above, in which
the shaft is formed of a metal, and electrically fixed at ground potential.

(6)

The handheld instrument for endoscope surgery according to any one of (1) to (5), further including
a protective member that is a tubular member formed of a metal and covers the signal wiring.

(7)

The handheld instrument for endoscope surgery according to (6) above, in which
the protective member is electrically fixed at ground potential.

(8)

The handheld instrument for endoscope surgery according to any one of (1) to (4) above, further including
a protective member including a metal layer covering the signal wiring, and a protective layer covering the metal layer.

(9)

The handheld instrument for endoscope surgery according to (8) above, in which
the metal layer is electrically fixed at ground potential.

(10)

The handheld instrument for endoscope surgery according to any one of (1) to (9) above, in which
the handle further includes a rotation knob for rotating the shaft,
the rotation knob has an introduction hole, and
the signal wiring is introduced from the handle into the shaft via the introduction hole.

(11)

The handheld instrument for endoscope surgery according to (1) above, in which
the signal wiring is a flexible printed circuit board,
the handheld instrument for endoscope surgery further including a sealing member for sealing a portion of the signal wiring led out from the jaw,
the signal wiring is placed on an outer peripheral surface of the shaft,
the handle further includes a rotation knob for rotating the shaft,
the rotation knob has an introduction hole, and
the signal wiring is introduced from the handle into the shaft via the introduction hole.

(12)

The handheld instrument for endoscope surgery according to any one of (1) to (11) above, in which
the phased array ultrasonic sensor includes an acoustic lens formed of a material having an acoustic impedance of not less than 1.35 M rayls and not more than 1.74 M rayls.

(13)

The handheld instrument for endoscope surgery according to any one of (1) to (12) above, in which
the phased array ultrasonic sensor includes a backing layer formed of a material having an acoustic impedance of 2.05 M rayls.

(14)

The handheld instrument for endoscope surgery according to any one of (1) to (13) above, in which
the phased array ultrasonic sensor includes a backing layer formed of a material having an acoustic attenuation constant of not less than 2.29 dB/MHz/mm.

(15)

The handheld instrument for endoscope surgery according to any one of (1) to (14) above, in which
the backing layer is formed of polyurethane.

(16)

The handheld instrument for endoscope surgery according to any one of (1) to (15) above, in which
the phased array ultrasonic sensor includes an acoustic lens formed of a material having an acoustic impedance of not less than 1.35 M rayls and not more than 1.74 M rayls, and a backing layer formed of a material having an acoustic impedance of not more than 2.05 M rayls.

(17)

The handheld instrument for endoscope surgery according to any one of (1) to (16) above, in which
the jaw includes
a jaw main body connected to the shaft,
a casing that is mounted on the jaw main body and houses phased array ultrasonic sensor, and
a tissue pad mounted on a side of the jaw main body opposite to the casing.

(18)

The handheld instrument for endoscope surgery according to (17) above, in which
at least one of the casing and the tissue pad is mounted on the jaw main body by adhesion.

(19)

The handheld instrument for endoscope surgery according to (17) above, in which the jaw main body has a recessed portion provided to at least one of a side of the casing and a side of the tissue pad, and the at least one of the casing and the tissue pad has a projecting portion engaging with the recessed portion.

(20)

The handheld instrument for endoscope surgery according to any one of (1) to (16) above, in which the jaw includes a jaw main body connected to the shaft, a thermal contraction tube that is mounted on the jaw main body and covers the phased array ultrasonic sensor therein, and a tissue pad mounted on an opposite side of the jaw main body from the thermal contraction tube.

(21)

The handheld instrument for endoscope surgery according to (20) above, in which at least one of the thermal contraction tube and the tissue pad is mounted on the jaw main body by adhesion.

(22)

The handheld instrument for endoscope surgery according to (20) above, in which the jaw main body has a side that is opposite to the shaft and divided into two or more ends, and the thermal contraction tube covers the phased array ultrasonic sensor and one end of the jaw main body therein.

(23)

The handheld instrument for endoscope surgery according to any one of (1) to (16) above, in which the jaw includes a jaw main body that is connected to the shaft and houses the phased array ultrasonic sensor, and a tissue pad mounted on the jaw main body.

(24)

The handheld instrument for endoscope surgery according to any one of (1) to (23) above, in which the jaw includes a jaw main body connected to the shaft, and a tissue pad and casing that is mounted on the jaw main body and houses the phased array ultrasonic sensor, a part or all of the tissue pad and casing being formed of polyurethane.

(25)

The handheld instrument for endoscope surgery according to (24) above, in which the jaw main body is formed of a metal.

(26)

The handheld instrument for endoscope surgery according to (24) above, in which the tissue pad and casing includes a tissue pad portion formed of polyurethane, and a casing portion that is formed of a material different from polyurethane and houses the phased array ultrasonic sensor.

(27)

The handheld instrument for endoscope surgery according to any one of (1) to (16) above, in which the jaw includes a supporting member having a rigidity higher than that of the phased array ultrasonic sensor.

(28)

The handheld instrument for endoscope surgery according to any one of (17), (20), (23), and (24) above, in which the jaw includes a supporting member having a rigidity higher than that of the phased array ultrasonic sensor.

REFERENCE SIGNS LIST 100 handheld instrument for endoscope surgery
110 handle
112 rotation knob
113 operation mechanism
130 shaft
131 jaw driving pipe
134 protective member
136 protective member
140 signal wiring
150 jaw
154 ultrasonic transducer array
1000 ultrasonic sensor
1100, 1200, 1300, 1400, 1500, 1600, 1700 movable jaw
1110, 1210, 1310, 1410, 1510, 1610, 1710 jaw main body
1120, 1320 casing
1220, 1420 thermal contraction tube
1130, 1230, 1330, 1430, 1530 tissue pad
1620, 1720 tissue pad and casing
1630, 1730 supporting member

The invention claimed is:

1. A handheld instrument for endoscope surgery, comprising:
   a protective member;
   a shaft enclosed by the protective member;
   a jaw at a first end of the shaft, wherein the jaw includes a jaw main body, a movable jaw and a probe configured to hold a biological tissue;
   a handle at a second end of the shaft, wherein the handle is configured to operate the jaw;
   a phased array ultrasonic sensor on the jaw, wherein the phased array ultrasonic sensor has an imaging function;
   a thermal contraction tube mounted on the jaw main body;
   a supporting member inside the thermal contraction tube, wherein the thermal contraction tube houses the supporting member and the phased array ultrasonic sensor;
   a signal wiring between the protective member and an outer peripheral surface of the shaft, wherein the signal wiring is configured to connect the phased array ultrasonic sensor and the handle;
   a sealing member configured to seal a first portion of the signal wiring led out from the jaw, wherein
      the sealing member has an opening, and
      the signal wiring is introduced into the opening of the sealing member from an outer surface of the movable jaw; and
   a covering member configured to cover the first portion of the signal wiring in the opening of the sealing member and a second portion of the signal wiring between the shaft and the jaw.

2. The handheld instrument for the endoscope surgery according to claim 1, wherein the signal wiring is a flexible printed circuit board.

3. The handheld instrument for the endoscope surgery according to claim 1, wherein
   the shaft is made of a metal, and
   the shaft is electrically fixed at ground potential.

4. The handheld instrument for the endoscope surgery according to claim 1, wherein
   the protective member is made of a metal,
   the protective member is tubular in shape, and
   the protective member is configured to cover the signal wiring.

5. The handheld instrument for the endoscope surgery according to claim 4, wherein the protective member is electrically fixed at ground potential.

6. The handheld instrument for the endoscope surgery according to claim 4, wherein the protective member further includes:
a metal layer that covers the signal wiring; and
a protective layer that covers the metal layer.

7. The handheld instrument for the endoscope surgery according to claim 6, wherein the metal layer of the protective member is electrically fixed at ground potential.

8. The handheld instrument for the endoscope surgery according to claim 1, wherein the handle further includes a rotation knob configured to rotate the shaft, wherein
the rotation knob has an introduction hole, and
the signal wiring is introduced from the handle into the shaft via the introduction hole.

9. The handheld instrument for the endoscope surgery according to claim 1, wherein the phased array ultrasonic sensor includes an acoustic lens made of a material having an acoustic impedance in a range between 1.35 M rayls and 1.74 M rayls.

10. The handheld instrument for the endoscope surgery according to claim 1, wherein the phased array ultrasonic sensor includes a backing layer made of a material having an acoustic impedance of 2.05 M rayls.

11. The handheld instrument for the endoscope surgery according to claim 10, wherein the material of the backing layer has an acoustic attenuation constant of at least 2.29 dB/MHz/mm.

12. The handheld instrument for the endoscope surgery according to claim 10, wherein the backing layer is made of polyurethane.

13. The handheld instrument for the endoscope surgery according to claim 1, wherein the phased array ultrasonic sensor includes:
an acoustic lens made of a material having an acoustic impedance in a range between 1.35 M rayls and 1.74 M rayls; and
a backing layer made of a material having an acoustic impedance less than 2.05 M rayls.

14. The handheld instrument for the endoscope surgery according to claim 1, wherein
the jaw main body is connected to the shaft, and
the handheld instrument-further comprising:
a casing on the jaw main body; and
a tissue pad on a side of the jaw main body opposite to the casing.

15. The handheld instrument for the endoscope surgery according to claim 14, wherein at least one of the casing or the tissue pad is mounted on the jaw main body by adhesion.

16. The handheld instrument for the endoscope surgery according to claim 14, wherein
the jaw main body has a recessed portion in at least one of a side of the casing or a side of the tissue pad, and
the at least one of the casing or the tissue pad has a projecting portion that engages with the recessed portion.

17. The handheld instrument for the endoscope surgery according to claim 14, wherein
the thermal contraction tube covers the phased array ultrasonic sensor, and
the tissue pad is on an opposite side of the jaw main body from the thermal contraction tube.

18. The handheld instrument for the endoscope surgery according to claim 17, wherein the tissue pad is mounted on the jaw main body by adhesion.

19. The handheld instrument for the endoscope surgery according to claim 17, wherein
the jaw main body has a side that is opposite to the shaft and divided into at least two ends, and
the thermal contraction tube is further configured to cover one end of the at least two ends of the jaw main body.

20. The handheld instrument for the endoscope surgery according to claim 14, wherein
the tissue pad is further configured to hold the biological tissue together with the probe in a case where the movable jaw is closed, and
a part of or an entire surface of the tissue pad and a part of or an entire surface of the casing of the phased array ultrasonic sensor are made of polyurethane.

21. The handheld instrument for the endoscope surgery according to claim 14, wherein the jaw main body is made of a metal.

22. The handheld instrument for the endoscope surgery according to claim 20, wherein
the tissue pad includes a tissue pad portion made of polyurethane, and
the casing of the phased array ultrasonic sensor includes a casing portion made of a material different from polyurethane.

23. The handheld instrument for the endoscope surgery according to claim 1, wherein the jaw includes the supporting member having a rigidity higher than that of the phased array ultrasonic sensor.

24. The handheld instrument for the endoscope surgery according to claim 1, wherein the covering member is further configured to deform based on a position of the movable jaw.

* * * * *